United States Patent

Ishihara et al.

[11] Patent Number: 5,925,658
[45] Date of Patent: Jul. 20, 1999

[54] OPTICALLY ACTIVE THIAZOLIDINONE DERIVATIVE

[75] Inventors: Sadao Ishihara, Hasuda; Fujio Saito, Urayasu; Yasuo Ohhata, Tokyo; Shigeki Miyake, Mitaka; Ryosuke Yorikane, Toda; Norio Fukuda, Tokyo, all of Japan

[73] Assignee: Sankyo Company, Limited, Tokyo, Japan

[21] Appl. No.: 08/923,745

[22] Filed: Sep. 2, 1997

Related U.S. Application Data

[63] Continuation-in-part of application No. PCT/JP96/00487, Mar. 1, 1996.

[30] Foreign Application Priority Data

Mar. 2, 1995 [JP] Japan .................................. 7-042237
Oct. 27, 1995 [JP] Japan .................................. 7-279951

[51] Int. Cl.⁶ ........................ A61K 31/425; C07D 277/14
[52] U.S. Cl. .................................. 514/369; 548/188
[58] Field of Search ............................... 514/369; 548/188

[56] References Cited

U.S. PATENT DOCUMENTS

| | | | |
|---|---|---|---|
| 3,957,750 | 5/1976 | MacLeay et al. ........................ | 260/174 |
| 4,200,640 | 4/1980 | Nagano et al. .......................... | 424/266 |
| 4,565,824 | 1/1986 | Wehinger et al. ....................... | 514/356 |
| 4,652,516 | 3/1987 | Ichijima et al. ......................... | 430/544 |
| 4,698,297 | 10/1987 | Ichijima et al. ........................ | 430/383 |
| 4,758,312 | 7/1988 | Hunt et al. ............................... | 204/1 T |
| 4,780,560 | 10/1988 | Kumonaka et al. .................... | 558/482 |
| 4,801,596 | 1/1989 | Simon et al. ............................ | 514/327 |
| 4,863,949 | 9/1989 | Simon et al. ............................ | 514/418 |
| 4,891,380 | 1/1990 | Williams et al. ........................ | 514/353 |
| 4,923,886 | 5/1990 | Shiokawa et al. ...................... | 514/365 |
| 4,968,598 | 11/1990 | Nakamura et al. ..................... | 430/617 |
| 5,010,093 | 4/1991 | Shiokawa et al. ...................... | 514/374 |
| 5,030,641 | 7/1991 | Simon et al. ............................ | 514/345 |
| 5,037,849 | 8/1991 | Simon et al. ............................ | 514/509 |
| 5,049,694 | 9/1991 | Bron et al. ............................... | 558/480 |
| 5,057,317 | 10/1991 | Iida ........................................... | 424/423 |
| 5,095,027 | 3/1992 | Goldberg et al. ........................ | 514/369 |
| 5,211,943 | 5/1993 | Azuma et al. ........................... | 424/448 |
| 5,280,031 | 1/1994 | Simon et al. ............................. | 514/331 |
| 5,298,516 | 3/1994 | Ishihara et al. .......................... | 514/369 |
| 5,306,724 | 4/1994 | Goldberg ................................. | 514/369 |
| 5,356,918 | 10/1994 | Ishihara et al. .......................... | 514/376 |
| 5,385,922 | 1/1995 | Bron et al. ............................... | 514/365 |
| 5,399,573 | 3/1995 | Garner et al. ............................ | 514/369 |
| 5,580,893 | 12/1996 | Ishihara et al. .......................... | 514/378 |
| 5,780,489 | 7/1998 | Brooks ..................................... | 514/369 |

FOREIGN PATENT DOCUMENTS 2-28167   1/1990   Japan .
5-213910  8/1993   Japan .

*Primary Examiner*—Laura L. Stockton
*Attorney, Agent, or Firm*—Frishauf, Holtz, Goodman, Langer & Chick, P.C.

[57] ABSTRACT

An optically active thiazolidinone derivative having the general formula:

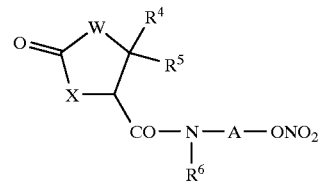

(II)

wherein: $R^1$ represents a hydrogen atom, a $C_1$–$C_4$ alkyl group, a phenyl group, a substituted phenyl group (said substituent represents $C_1$–$C_4$ alkyl, $C_1$–$C_4$ alkoxy or halogen), a phenyl-$C_1$–$C_2$ alkyl group or a substituted phenyl-$C_3$–$C_2$ alkyl group (the substituent of said phenyl represents $C_1$–$C_4$ alkyl, $C_1$–$C_4$ alkoxy or halogen); $R^2$ represents a $C_1$–$C_6$ alkyl group; and n represents 1 or 2]. Effect The optically active thiazolidinone derivative of the present invention has excellent anti-angina pectoris action and is useful as a preventive agent or a therapeutic agent for angina pectoris.

23 Claims, No Drawings

OPTICALLY ACTIVE THIAZOLIDINONE DERIVATIVE

This application is a continuation-in-part application of International Application PCT/JP96/00487 filed Mar. 1, 1996.

TECHNICAL FIELD

The present invention relates to optically active thiazolidinone derivatives having an excellent collateral vessel dilating action and an anti-angina pectoris action, a composition for prevention or therapy of angina pectoris comprising them as an active ingredient, use of them for producing a pharmaceutical preparation for prevention or therapy of angina pectoris, a preventive or therapeutic method for angina pectoris comprising administering a pharmacologically effective amount of them to a mammal or a preparation process thereof; or a composition for prevention or therapy of an ulcerative disease comprising thia- or oxazolidinone derivatives as an active ingredient, use of them for producing a pharmaceutical preparation for prevention or therapy of an ulcerative disease or a preventive or therapeutic method for an ulcerative disease comprising administering a pharmacologically effective amount of them to a mammal.

PRIOR ART

At present, as a therapeutic agent for cardiovascular diseases, particularly for angina pectoris, nitroglycerin is most frequently used clinically. However, nitroglycerin easily undergoes the first-pass effect and has a defect that duration of its action is short. Meanwhile, headache, vertigo and tachycardia due to reduction in blood pressure appear as side effects. In view of such background, there has been demanded a therapeutic agent for angina pectoris with prolonged actions which clinically does not undergo the first-pass effect.

The present inventors have found, as a means for solving the above problem, a compound having a thia- or oxazolidinone skelton, for example, compound A having the following formula:

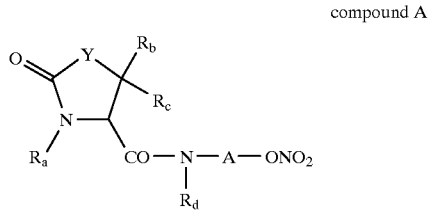

compound A (wherein Ra, Rb, Rc and Rd represent a hydrogen atom, etc., A represents a $C_2$–$C_6$ alkylene group and Y represents an oxygen atom or a sulfur atom)
(for example, Japanese Unexamined Patent Publication (KOKAI) No. Hei 5-213910). However, an anti-ulcerative action of these compounds has not been known at all.

DISCLOSURE OF THE INVENTION

The present inventors made further studies and have found that compounds having an optically active thiazolidinone skelton have an excellent collateral vessel dilating action which is prolonged and exhibit less side effects, the compounds are useful as a preventive agent or a therapeutic agent for angina pectoris (particularly a therapeutic agent for angina pectoris) and the compounds have excellent stability to accomplish the present invention. Moreover, the present inventors made studies on pharmacological effects of the compounds having a thia- or oxazolidinone skelton and have also found that these compounds have an excellent anti-ulcerative action and the compounds are useful as a preventive agent or a therapeutic agent for an ulcerative disease (particularly a therapeutic agent for an ulcerative disease).

The present invention provides optically active thiazolidinone derivatives, a composition for prevention or therapy of angina pectoris comprising them as an active ingredient, use of them for producing a pharmaceutical preparation for prevention or therapy of angina pectoris, a preventive or therapeutic method for angina pectoris comprising administering a pharmacologically effective amount of them to a mammal or a preparation process thereof; or a composition for prevention or therapy of an ulcerative disease comprising thia- or oxazolidinone derivatives as an active ingredient, use of them for producing a pharmaceutical preparation for prevention or therapy of an ulcerative disease or a preventive or therapeutic method for an ulcerative disease comprising administering a pharmacologically effective amount of them to a mammal.

CONSTITUTION OF THE INVENTION

The optically active thiazolidinone derivatives of the present invention have the general formula:

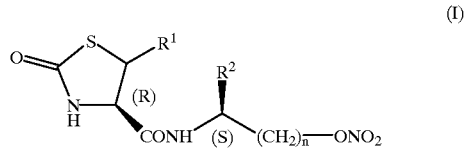

(I)

In the above formula, $R^1$ represents a hydrogen atom, a $C_1$–$C_4$ alkyl group, a phenyl group, a substituted phenyl group (the substituent represents $C_1$–$C_4$ alkyl, $C_1$–$C_4$ alkoxy or halogen), a phenyl-$C_1$–$C_2$ alkyl group or a substituted phenyl-$C_1$–$C_2$ alkyl group (the substituent of the phenyl represents $C_1$–$C_4$ alkyl, $C_1$–$C_4$ alkoxy or halogen);

$R^2$ represents a $C_1$–$C_6$ alkyl group; and n represents 1 or 2.

The thia- or oxazolidinone derivatives which are an active ingredient of a preventive agent or a therapeutic agent for an ulcerative disease have the general formula:

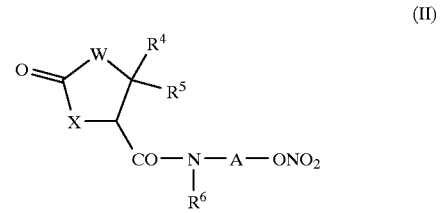

(II)

In the above formula, W represents a sulfur atom or an oxygen atom and X represents a group having the formula: —N($R^3$)— or X represents a sulfur atom or an oxygen atom and W represents a group having the formula: —N($R^3$)—;

$R^3$ represents a hydrogen atom, a $C_1$–$C_6$ alkyl group or an aryl-$C_1$–$C_4$ alkyl group;

$R^4$ and $R^5$ may be the same or different and represents a hydrogen atom, a $C_1$–$C_6$ alkyl group, an aryl-$C_1$–$C_4$ alkyl group, an aryl group, a 5- or 6-membered aromatic heterocyclic group containing 1 to 3 hetero atoms selected from the group consisting of nitrogen atoms, oxygen atoms and sulfur atoms, which may be optionally condensed with a benzene ring or a 5- or 6-membered aromatic heterocyclic group containing 1 to 3 hetero atoms selected from the group consisting of nitrogen atoms, oxygen atoms and sulfur atoms which may be optionally substituted and condensed with a benzene ring (the substituent represents $C_1$–$C_6$ alkyl, amino, mono-$C_1$–$C_6$ alkylamino or di-$C_1$–$C_6$ alkylamino);

$R^6$ represents a hydrogen atom, a $C_1$–$C_6$ alkyl group or an aryl-$C_1$–$C_4$ alkyl group;

A represents a $C_2$–$C_6$ alkylene group or a substituted $C_2$–$C_6$ alkylene group (the substituent represents a carboxyl group, a $C_1$–$C_6$ alkoxycarbonyl group or an aryloxycarbonyl group); and the above-mentioned aryl represents $C_6$–$C_{10}$ aryl or substituted $C_6$–$C_{10}$aryl (the substituent represents $C_1$–$C_6$ alkyl, $C_1$–$C_6$ alkoxy, hydroxy, halogen, amino, mono-$C_1$–$C_6$ alkylamino, di-$C_1$–$C_6$ alkylamino or nitro).

The $C_1$–$C_4$ alkyl group of $R^1$ etc., or the alkyl moiety of the $C_1$–$C_4$ alkoxy group included in $R^1$ may include, for example, a methyl, ethyl, propyl, isopropyl, butyl, s-butyl, isobutyl and t-butyl group, preferably a $C_1$–$C_3$ alkyl group, more preferably a $C_1$–$C_2$ alkyl group, and particularly preferably a methyl group.

The halogen atom included in $R^1$ may include, for example, a fluorine, chlorine, bromine and iodine atom, and preferably a fluorine atom or a chlorine atom.

The phenyl-$C_1$–$C_2$ alkyl group of $R^1$ may include preferably benzyl group or phenethyl group, and more preferably benzyl group.

The $C_1$–$C_6$ alkyl group of $R^2$ may include, for example, a methyl, ethyl, propyl, isopropyl, butyl, s-butyl, isobutyl, t-butyl, pentyl and hexyl group, preferably a $C_1$–$C_4$ alkyl group, more preferably a methyl, ethyl, propyl, isopropyl, butyl or isobutyl group, still more preferably a methyl, propyl, butyl or isobutyl group, and particularly preferably a methyl group.

The $C_1$–$C_6$ alkyl group of $R^3$, $R^4$, $R^5$, $R^6$, etc., or the alkyl moiety of the $C_1$–$C_6$ alkoxy group or the $C_1$–$C_6$ alkylamino group included in $R^3$, A, etc., may include the above group, preferably a $C_1$–$C_4$ alkyl group, more preferably a $C_1$–$C_2$ alkyl group, and particularly preferably a methyl group.

The aryl moiety of the aryl-$C_1$–$C_4$ alkyl group of $R^3$, $R^4$, $R^5$ and $R^6$ may include the group described below and the alkyl moiety may include the above group, and may include, for example, a benzyl, phenethyl, 2-phenylpropyl, 3-phenylpropyl, 4-phenylbutyl, diphenylmethyl, 1-naphthylmethyl and 2-naphthylmethyl group, preferably phenyl-($C_1$–$C_4$ alkyl) group, more preferably a benzyl group or a phenethyl group, and particularly preferably a benzyl group.

The aryl group of $R^4$ and $R^5$ or the aryl moiety of the aryloxycarbonyl group included in A may include the above group, and preferably a phenyl group.

The halogen of the substituent of the aryl group of $R^4$ and $R^5$ may include the above group, and preferably a fluorine atom or a chlorine atom.

The 5- or 6-membered aromatic heterocyclic group containing 1 to 3 hetero atoms selected from the group consisting of nitrogen atoms, oxygen atoms and sulfur atoms which may be optionally condensed with a benzene ring may include, for example, furyl, thienyl, pyrrolyl, oxazolyl, isoxazolyl, thiazolyl, isothiazolyl, imidazolyl, pyrazolyl, pyridyl, pyridazinyl, pyrimidinyl, indolyl, quinolyl and quinazolinyl, preferably furyl, thienyl, oxazolyl, isoxazolyl, thiazolyl, isothiazolyl or pyridyl, more preferably a furyl, thienyl or pyridyl group, and particularly preferably a furyl group or a thienyl group.

The alkylene moiety of the $C_2$–$C_6$ alkylene group of A may include, for example, ethylene, methylethylene, trimethylene, tetramethylene, pentamethylene and hexamethylene, preferably a $C_2$–$C_4$ alkylene group, and particularly preferably an ethylene group or a methylethylene group.

In the compound (II), those containing a carboxy or phenol moiety may form salts with a base. Such salts may include, for example, a salt with an alkali metal such as lithium, sodium and potassium, a salt with an alkaline earth metal such as barium and calcium, a salt with other metals such as magnesium and aluminum, a salt with an organic amine such as dicyclohexylamine and a salt with a basic amino acid such as lysine and arginine, and preferably a salt with an alkali metal. Meanwhile, the compound (II) containing amino or alkylamino moieties can form salts with an acid. Such salts may include, for example, a salt with an inorganic acid such as hydrochloric acid, bromic acid, sulfuric acid, phosphoric acid and carbonic acid, a salt with a carboxylic acid such as acetic acid, fumaric acid, maleic acid, oxalic acid, malonic acid, succinic acid, citric acid, malic acid and benzoic acid, a salt with a sulfonic acid such as methanesulfonic acid, ethanesulfonic acid, benzenesulfonic acid and toluenesulfonic acid and a salt with an acidic amino acid such as glutamic acid and aspartic acid, and preferably a salt with hydrochloric acid or a carboxylic acid.

Further, the present invention includes hydrates of the compound (I) and in the case where an asymmetric carbon exists in a molecule of the compound (II), the present invention includes a racemic modification and an optically active substance and also includes the compound (II) or hydrates of a salt thereof.

Meanwhile, the compound (I) included in the compound (II) also has an excellent anti-ulcerative action.

The compound having the general formula (I) may include preferably 1) a compound in which $R^1$ is a hydrogen atom, a $C_1$–$C_4$ alkyl group, a phenyl group, a substituted phenyl group (the substituent is methyl, methoxy, fluorine or chlorine), a benzyl group, a substituted benzyl group (the substituent is methyl, methoxy, fluorine or chlorine), a phenethyl group or a substituted phenethyl group (the substituent is methyl, methoxy, fluorine or chlorine), 2) a compound in which $R^1$ is a hydrogen atom, a methyl group, a 4-methoxyphenyl group or a benzyl group, 3) a compound in which $R^1$ is a hydrogen atom, 4) a compound in which $R^2$ is a $C_1$–$C_4$ alkyl group, 5) a compound in which $R^2$ is a methyl group, an ethyl group, a propyl group, an isopropyl group, a butyl group or an isobutyl group, 6) a compound in which $R^2$ is a methyl group, a propyl group, a butyl group or an isobutyl group, 7) a compound in which $R^2$ is a methyl group, and 8) a compound in which n is 1.

Meanwhile, an optional combination of the compound selected arbitrarily from the group consisting of 1)-3), 4)-7) and 8) is preferred and may include, for example, the following compounds.

9) a compound in which $R^1$ is a hydrogen atom, a $C_1$–$C_4$ alkyl group, a phenyl group, a substituted phenyl group (the substituent is methyl, methoxy, fluorine or chlorine), a benzyl group, a substituted benzyl group (the substituent is methyl, methoxy, fluorine or chlorine), a phenethyl group or a substituted phenethyl group (the substituent is methyl, methoxy, fluorine or chlorine);
$R^2$ is a $C_1$–$C_4$ alkyl group; and
n is 1, 10) a compound in which $R^1$ is a hydrogen atom, a methyl group, a 4-methoxyphenyl group or a benzyl group;
$R^2$ is a methyl group, an ethyl group, a propyl group, an isopropyl group, a butyl group or an isobutyl group; and
n is 1, 11) a compound in which $R^1$ is a hydrogen atom;
$R^2$ is a methyl group, a propyl group, a butyl group or an isobutyl group; and
n is 1, and 12) a compound in which $R^1$ is a hydrogen atom; and
$R^2$ is a methyl group.

Meanwhile, the compound having the above general formula (II) may include preferably 13) a compound in which $R^3$ is a hydrogen atom, a $C_1$–$C_4$ alkyl group, a benzyl group or a phenethyl group, 14) a compound in which $R^3$ is a hydrogen atom, a methyl group or a benzyl group, 15) a compound in which W is a sulfur atom or an oxygen atom and X is a group having the formula: —N($R^3$)— (wherein $R^3$ is a hydrogen atom) or
X is a sulfur atom and W is a group having the formula: —N($R^3$)— (wherein $R^3$ is a hydrogen atom), 16) a compound in which W is a sulfur atom or an oxygen atom and X is a group having the formula: —N$R^3$— (wherein $R^3$ is a hydrogen atom), 17) a compound in which $R^4$ and $R^5$ may be the same or different and each is a hydrogen atom, a $C_1$–$C_4$ alkyl group, a phenyl-$C_1$–$C_4$ alkyl group, a substituted phenyl-$C_1$–$C_4$ alkyl group (the substituent of the phenyl is $C_3$–$C_4$ alkyl, $C_1$–$C_4$ alkoxy, hydroxy, halogen or nitro), a naphthylmethyl group, a phenyl group, a substituted phenyl group (the substituent is $C_1$–$C_4$ alkyl, $C_1$–$C_4$ alkoxy, hydroxy, halogen or nitro), a naphthyl group or an unsubstituted or a $C_3$–$C_4$ alkyl-substituted furyl, thienyl, pyridyl, oxazolyl, thiazolyl, isoxazolyl or isothiazolyl group, 18) a compound in which $R^4$ and $R^5$ may be the same or different and each is a hydrogen atom, a methyl group, a benzyl group, a substituted benzyl group (the substituent is methyl, methoxy, hydroxy, fluoro or chloro), a phenethyl group, a substituted phenethyl group (the substituent is methyl, methoxy, hydroxy, fluoro or chloro), a phenyl group, a substituted phenyl group (the substituent is methyl, methoxy, hydroxy, fluoro or chloro), a furyl group, a thienyl group or a pyridyl group, 19) a compound in which $R^4$ is a hydrogen atom, a methyl group, a benzyl group, a substituted benzyl group (the substituent is methyl, methoxy or hydroxy), a phenyl group or a substituted phenyl group (the substituent is methyl, methoxy or hydroxy); and
$R^5$ is a hydrogen atom, 20) a compound in which $R^4$ is a hydrogen atom, a methyl group, a benzyl group, a phenyl group or a methoxyphenyl group; and
$R^5$ is a hydrogen atom, 21) a compound in which $R^4$ is a hydrogen atom, a methyl group, a benzyl group or a 4-methoxyphenyl group; and
$R^5$ is a hydrogen atom, 22) a compound in which $R^4$ is a hydrogen atom; and
$R^5$ is a hydrogen atom, 23) a compound in which $R^6$ is a hydrogen atom, a $C_1$–$C_4$ alkyl group, a benzyl group or a phenethyl group, 24) a compound in which $R^6$ is a hydrogen atom, a methyl group or a benzyl group, 25) a compound in which $R^6$ is a hydrogen atom, 26) a compound in which A is a $C_2$–$C_4$ alkylene group, a carboxy-$C_2$–$C_4$ alkylene group or a $C_1$–$C_4$ alkoxycarbonyl-$C_2$–$C_4$ alkylene group, 27) a compound in which A is a $C_2$–$C_4$ alkylene group, or 28) a compound in which A is an ethylene group or a 1-methylethylene group.

Meanwhile, an optional combination of the compound selected arbitrarily from the group consisting of 13)-16), 17)-22), 23)-25) and 26)-28) is also preferred and may include, for example, the following compounds:

29) a compound in which $R^3$ is a hydrogen atom, a $C_1$–$C_4$ alkyl group, a benzyl group or a phenethyl group;
$R^4$ and $R^5$ may be the same or different and each is a hydrogen atom, a $C_1$–$C_4$ alkyl group, a phenyl-$C_1$–$C_4$ alkyl group, a substituted phenyl-$C_1$–$C_4$ alkyl group (the substituent of the phenyl is $C_1$–$C_4$ alkyl, $C_1$–$C_4$ alkoxy, hydroxy, halogen or nitro), a naphthylmethyl group, a phenyl group, a substituted phenyl group (the substituent is $C_1$–$C_4$ alkyl, $C_1$–$C_4$ alkoxy, hydroxy, halogen or nitro), a naphthyl group or an unsubstituted or a $C_1$–$C_4$ alkyl-substituted furyl, thienyl, pyridyl, oxazolyl, thiazolyl, isoxazolyl or isothiazolyl group;
$R^6$ is a hydrogen atom, a $C_1$–$C_4$ alkyl group, a benzyl group or a phenethyl group; and
A is a $C_2$–$C_4$ alkylene group, a carboxy-$C_2$–$C_4$ alkylene group or a $C_1$–$C_4$ alkoxycarbonyl-$C_2$-$C_4$ alkylene group, 30) a compound in which $R^3$ is a hydrogen atom, a methyl group or a benzyl group;
$R^4$ and $R^5$ may be the same or different and each is a hydrogen atom, a methyl group, a benzyl group, a substituted benzyl group (the substituent is methyl, methoxy, hydroxy, fluoro or chloro), a phenethyl group, a substituted phenethyl group (the substituent is methyl, methoxy, hydroxy, fluoro or chloro), a phenyl group, a substituted phenyl group (the substituent is methyl, methoxy, hydroxy, fluoro or chloro), a furyl group, a thienyl group or a pyridyl group;
$R^6$ is a hydrogen atom, a methyl group or a benzyl group; and
A is a $C_2$–$C_4$ alkylene group, 31) a compound in which W is a sulfur atom or an oxygen atom and X is a group having the formula: —N$R_3$— (wherein $R^3$ is a hydrogen atom) or X is a sulfur atom and W is a group having the formula: —N$R^3$— (wherein $R_3$ is a hydrogen atom);
$R^4$ is a hydrogen atom, a methyl group, a benzyl group, a substituted benzyl group (the substituent is methyl, methoxy or hydroxy), a phenyl group or a substituted phenyl group (the substituent is methyl, methoxy or hydroxy);
$R^5$ is a hydrogen atom;

$R^6$ is a hydrogen atom; and

A is a $C_2$–$C_4$ alkylene group, 32) a compound in which W is a sulfur atom or an oxygen atom and X is a group having the formula: —$NR_3$— (wherein $R_3$ is a hydrogen atom);

$R^4$ is a hydrogen atom, a methyl group, a benzyl group, a phenyl group or a methoxyphenyl group;

$R^5$ is a hydrogen atom;

$R^6$ is a hydrogen atom; and

A is a $C_2$–$C_4$ alkylene group, 33) a compound in which W is a sulfur atom and X is a group having the formula: —$NR^3$— (wherein $R_3$ is a hydrogen atom);

$R^4$ is a hydrogen atom, a methyl group, a benzyl group or a 4-methoxyphenyl group;

$R^5$ is a hydrogen atom;

$R^6$ is a hydrogen atom; and

A is an ethylene group or a 1-methylethylene group, or 34) a compound in which W is a sulfur atom and X is a group having the formula: —$NR^3$— (wherein $R^3$ is a hydrogen atom);

$R^4$ is a hydrogen atom;

$R^5$ is a hydrogen atom;

$R^6$ is a hydrogen atom; and

A is an ethylene group or a 1-methylethylene group.

It has also been surprisingly found that the optically active thiazolidinone derivative of formula (I) is more stable on storage than its (4R),(1R)-isomer and mixtures of said isomers. In a further aspect of the present invention, there is provided a composition for preventing or treating angina pectoris containing the optically active thiazolidinone derivative of formula (I) as defined above in admixture with its (4R),(1R)-isomer of formula (I') as defined below, the amount of the (4R),(1R)-isomer of formula (I') being sufficiently small that said composition does not exhibit significant instability on storage:

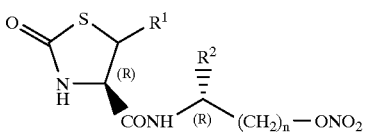

(I')

wherein $R^1$, $R^2$ and n are as defined above. Typically, the amount of the (4R),(1R)-isomer present in the active ingredient of said composition is less than 10% by weight, e.g. from 1 to 5% by weight.

There is also provided a method for the treatment or prophylaxis of angina pectoris comprising administering to a patient an effective amount of an active ingredient in admixture with a pharmacologically acceptable carrier or diluent, wherein said active ingredient contains greater than 90% by weight of an optically active thiazolidinone derivative of formula (I) as defined above in admixture with less than 10% by weight of its (4R),(1R)-isomer of formula (I') as defined above.

The preferred compound in the general formula (I) can be specifically exemplified in Table 1.

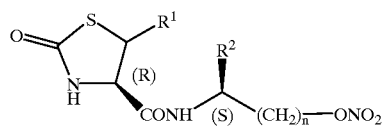

(I)

TABLE 1

| Compound No. | $R^1$ | $R^2$ | n |
|---|---|---|---|
| 1-1 | H | Me | 1 |
| 1-2 | Me | Me | 1 |
| 1-3 | Et | Me | 1 |
| 1-4 | Ph | Me | 1 |
| 1-5 | 4-Me-Ph | Me | 1 |
| 1-6 | 4-MeO-Ph | Me | 1 |
| 1-7 | 4-F-Ph | Me | 1 |
| 1-8 | 4-Cl-Ph | Me | 1 |
| 1-9 | Bz | Me | 1 |
| 1-10 | 4-Me-Bz | Me | 1 |
| 1-11 | 4-MeO-Bz | Me | 1 |
| 1-12 | 4-F-Bz | Me | 1 |
| 1-13 | 4-Cl-Bz | Me | 1 |
| 1-14 | $CH_2CH_2Ph$ | Me | 1 |
| 1-15 | H | Et | 1 |
| 1-16 | Me | Et | 1 |
| 1-17 | Ph | Et | 1 |
| 1-18 | 4-Me-Ph | Et | 1 |
| 1-19 | 4-MeO-Ph | Et | 1 |
| 1-20 | 4-F-Ph | Et | 1 |
| 1-21 | 4-Cl-Ph | Et | 1 |
| 1-22 | Bz | Et | 1 |
| 1-23 | 4-Me-Bz | Et | 1 |
| 1-24 | 4-MeO-Bz | Et | 1 |
| 1-25 | 4-F-Bz | Et | 1 |
| 1-26 | 4-Cl-Bz | Et | 1 |
| 1-27 | H | Pr | 1 |
| 1-28 | Me | Pr | 1 |
| 1-29 | Ph | Pr | 1 |
| 1-30 | 4-Me-Ph | Pr | 1 |
| 1-31 | 4-MeO-Ph | Pr | 1 |
| 1-32 | 4-F-Ph | Pr | 1 |
| 1-33 | 4-Cl-Ph | Pr | 1 |
| 1-34 | Bz | Pr | 1 |
| 1-35 | 4-Me-Bz | Pr | 1 |
| 1-36 | 4-MeO-Bz | Pr | 1 |
| 1-37 | 4-F-Bz | Pr | 1 |
| 1-38 | 4-Cl-Bz | Pr | 1 |
| 1-39 | H | Me | 2 |
| 1-40 | Me | Me | 2 |
| 1-41 | Ph | Me | 2 |
| 1-42 | 4-Me-Ph | Me | 2 |
| 1-43 | 4-MeO-Ph | Me | 2 |
| 1-44 | 4-F-Ph | Me | 2 |
| 1-45 | 4-Cl-Ph | Me | 2 |
| 1-46 | Bz | Me | 2 |
| 1-47 | 4-Me-Bz | Me | 2 |
| 1-48 | 4-MeO-Bz | Me | 2 |
| 1-49 | 4-F-Bz | Me | 2 |
| 1-50 | 4-Cl-Bz | Me | 2 |
| 1-51 | H | Et | 2 |
| 1-52 | Me | Et | 2 |
| 1-53 | Ph | Et | 2 |
| 1-54 | 4-Me-Ph | Et | 2 |
| 1-55 | 4-MeO-Ph | Et | 2 |
| 1-56 | Bz | Et | 2 |
| 1-57 | 4-Me-Bz | Et | 2 |
| 1-58 | 4-MeO-Bz | Et | 2 |
| 1-59 | H | $Pr^i$ | 1 |
| 1-60 | Me | $Pr^i$ | 1 |
| 1-61 | Ph | $Pr^i$ | 1 |
| 1-62 | 4-Me-Ph | $Pr^i$ | 1 |
| 1-63 | 4-MeO-Ph | $Pr^i$ | 1 |
| 1-64 | 4-F-Ph | $Pr^i$ | 1 |
| 1-65 | 4-Cl-Ph | $Pr^i$ | 1 |

TABLE 1-continued

| Compound No. | R¹ | R² | n |
|---|---|---|---|
| 1-66 | Bz | $Pr^i$ | 1 |
| 1-67 | 4-Me-Bz | $Pr^i$ | 1 |
| 1-68 | 4-MeO-Bz | $Pr^i$ | 1 |
| 1-69 | 4-F-Bz | $Pr^i$ | 1 |
| 1-70 | 4-Cl-Bz | $Pr^i$ | 1 |
| 1-71 | H | Bu | 1 |
| 1-72 | Me | Bu | 1 |
| 1-73 | Ph | Bu | 1 |
| 1-74 | 4-Me-Ph | Bu | 1 |
| 1-75 | 4-MeO-Ph | Bu | 1 |
| 1-76 | 4-F-Ph | Bu | 1 |
| 1-77 | 4-Cl-Ph | Bu | 1 |
| 1-78 | Bz | Bu | 1 |
| 1-79 | 4-Me-Bz | Bu | 1 |
| 1-80 | 4-MeO-Bz | Bu | 1 |
| 1-81 | 4-F-Bz | Bu | 1 |
| 1-82 | 4-Cl-Bz | Bu | 1 |
| 1-83 | H | $Bu^i$ | 1 |
| 1-84 | Me | $Bu^i$ | 1 |
| 1-85 | Fh | $Bu^i$ | 1 |
| 1-86 | 4-Me-Ph | $Bu^i$ | 1 |
| 1-87 | 4-MeO-Ph | $Bu^i$ | 1 |
| 1-88 | 4-F-Ph | $Bu^i$ | 1 |
| 1-89 | 4-Cl-Ph | $Bu^i$ | 1 |
| 1-90 | Bz | $Bu^i$ | 1 |
| 1-91 | 4-Me-Bz | $Bu^i$ | 1 |
| 1-92 | 4-MeO-Bz | $Bu^i$ | 1 |
| 1-93 | 4-F-Bz | $Bu^i$ | 1 |
| 1-94 | 4-Cl-Bz | $Bu^i$ | 1 |
| 1-95 | H | $Bu^s$ | 1 |
| 1-96 | Me | $Bu^s$ | 1 |
| 1-97 | Ph | $Bu^s$ | 1 |
| 1-98 | 4-Me-Ph | $Bu^s$ | 1 |
| 1-99 | 4-MeO-Ph | $Bu^s$ | 1 |
| 1-100 | Bz | $Bu^s$ | 1 |
| 1-101 | 4-Me-Bz | $Bu^s$ | 1 |
| 1-102 | 4-MeO-Bz | $Bu^s$ | 1 |
| 1-103 | H | $Bu^t$ | 1 |
| 1-104 | Me | $Bu^t$ | 1 |
| 1-105 | Ph | $Bu^t$ | 1 |
| 1-106 | 4-Me-Ph | $Bu^t$ | 1 |
| 1-107 | 4-MeO-Ph | $Bu^t$ | 1 |
| 1-108 | Bz | $Bu^t$ | 1 |
| 1-109 | 4-Me-Bz | $Bu^t$ | 1 |
| 1-110 | 4-MeO-Bz | $Bu^t$ | 1 |
| 1-111 | H | Pn | 1 |
| 1-112 | Me | Pn | 1 |
| 1-113 | Ph | Pn | 1 |
| 1-114 | 4-Me-Ph | Pn | 1 |
| 1-115 | 4-MeO-Ph | Pn | 1 |
| 1-116 | Bz | Pn | 1 |
| 1-117 | 4-Me-Bz | Pn | 1 |
| 1-118 | 4-MeO-Bz | Pn | 1 |
| 1-119 | H | Hx | 1 |
| 1-120 | Me | Hx | 1 |
| 1-121 | Ph | Hx | 1 |
| 1-122 | 4-Me-Ph | Hx | 1 |
| 1-123 | 4-MeO-Ph | Hx | 1 |
| 1-124 | Bz | Hx | 1 |
| 1-125 | 4-Me-Bz | Hx | 1 |
| 1-126 | 4-MeO-Bz | Hx | 1 |
| 1-127 | H | Pr | 2 |
| 1-128 | Me | Pr | 2 |
| 1-129 | Ph | Pr | 2 |
| 1-130 | 4-Me-Ph | Pr | 2 |
| 1-131 | 4-MeO-Ph | Pr | 2 |
| 1-132 | Bz | Pr | 2 |
| 1-133 | 4-Me-Bz | Pr | 2 |
| 1-134 | 4-MeO-Bz | Pr | 2 |
| 1-135 | H | $Pr^i$ | 2 |
| 1-136 | Me | $Pr^i$ | 2 |
| 1-137 | Ph | $Pr^i$ | 2 |
| 1-138 | 4-Me-Ph | $Pr^i$ | 2 |
| 1-139 | 4-MeO-Ph | $Pr^i$ | 2 |
| 1-140 | Bz | $Pr^i$ | 2 |
| 1-141 | 4-Me-Bz | $Pr^i$ | 2 |
| 1-142 | 4-MeO-Bz | $Pr^i$ | 2 |
| 1-143 | H | Bu | 2 |
| 1-144 | Me | Bu | 2 |
| 1-145 | Ph | Bu | 2 |
| 1-146 | 4-Me-Ph | Bu | 2 |
| 1-147 | 4-MeO-Ph | Bu | 2 |
| 1-148 | Bz | Bu | 2 |
| 1-149 | 4-Me-Bz | Bu | 2 |
| 1-150 | 4-MeO-Bz | Bu | 2 |
| 1-151 | H | $Bu^i$ | 2 |
| 1-152 | Me | $Bu^i$ | 2 |
| 1-153 | Ph | $Bu^i$ | 2 |
| 1-154 | 4-Me-Ph | $Bu^i$ | 2 |
| 1-155 | 4-MeO-Ph | $Bu^i$ | 2 |
| 1-156 | Bz | $Bu^i$ | 2 |
| 1-157 | 4-Me-Bz | $Bu^i$ | 2 |
| 1-158 | 4-MeO-Bz | $Bu^i$ | 2 |

In the above Table 1, the abbreviation indicates the following group.

| | |
|---|---|
| Bz | Benzyl |
| Bu | Butyl |
| $Bu^i$ | Isobutyl |
| $Bu^s$ | s-Butyl |
| $Bu^t$ | t-Butyl |
| Et | Ethyl |
| Hx | Hexyl |
| Me | Methyl |
| Ph | Phenyl |
| Pn | Pentyl |
| Pr | Propyl |
| $Pr^i$ | Isopropyl |

In the above Table 1, preferred are compounds of Compound Nos. 1-1, 1-2, 1-3, 1-6, 1-7, 1-9, 1-10, 1-11, 1-12, 1-13, 1-14, 1-15, 1-27, 1-28, 1-29, 1-30, 1-31, 1-32, 1-33, 1-34, 1-36, 1-39, 1-40, 1-43, 1-59, 1-60, 1-71, 1-72, 1-73, 1-74, 1-75, 1-78, 1-80, 1-83, 1-84, 1-85, 1-87, 1-90, 1-92, 1-95, 1-103, 1-111, 1-112, 1-116, 1-119, 1-120, 1-123, 1-124, 1-127, 1-143 and 1-151;

more preferred are compounds of Compounds Nos. 1-1, 1-2, 1-3, 1-6, 1-9, 1-10, 1-12, 1-14, 1-27, 1-28, 1-29, 1-31, 3-32, 1-33, 1-34, 1-36, 1-60, 1-71, 1-72, 1-73, 1-75, 1-78, 1-80, 1-83, 1-84, 1-85, 1-87, 1-90, 1-92, 1-95, 1-103, 1-111, 1-112, 1-116, 1-119, 1-120, 1-123, 1-124, 1-127, 1-143 and 1-151;

and particularly preferred are the compounds of

Compound No. 1-1: (4R)-N-[(1S)-1-methyl-2-nitroxyethyl]-2-oxothiazolidin-4-yl-carboxamide, Compound No. 1-2: (4R)-N-[(1S)-1-methyl-2-nitroxyethyl]-5-methyl-2-oxothiazolidin-4-yl-carboxamide, Compound No. 1-6: (4R)-N-[(1S)-1-methyl-2-nitroxyethyl]-5-(4-methoxyphenyl)-2-oxothiazolidin-4-yl-carboxamide, Compound No. 1-9: (4R)-N-[(1S)-1-methyl-2-nitroxyethyl]-5-benzyl-2-oxothiazolidin-4-yl-carboxamide, Compound No. 1-15: (4R)-N-[(1S)-1-ethyl-2-nitroxyethyl]-2-oxothiazolidin-4-yl-carboxamide, Compound No. 1-27: (4R)-N-[(1S)-1-propyl-2-nitroxyethyl]-2-oxothiazolidin-4-yl-carboxamide, Compound No. 1-28: (4R)-N-[(1S)-1-propyl-2-nitroxyethyl]-5-methyl-2-oxothiazolidin-4-yl-carboxamide, Compound No. 1-31: (4R)-N-[(1S)-1-propyl-2-nitroxyethyl]-5-(4-methoxyphenyl)-2-oxothiazolidin-4-yl-carboxamide, Compound No. 1-34: (4R)-N-[(1S)-1-propyl-2-nitroxyethyl]-5-benzyl-2-oxothiazolidin-4-yl-carboxamide, Compound No. 1-71: (4R)-N-[(1S)-1-butyl-2-nitroxyethyl]-2-oxothiazolidin-4-yl-carboxamide, Compound No. 1-72: (4R)-N-[(1S) -1-butyl-2-nitroxyethyl]-5-methyl-2-oxothiazolidin-4-yl-carboxamide, Compound No. 1-75: (4R)-N-[(1S)-1-butyl-2-nitroxyethyl]-5-(4-methoxyphenyl)-2-oxothiazolidin-4-yl-carboxamide, Compound No. 1-78: (4R)-N-[(1S)-1-butyl-2-nitroxyethyl]-5-benzyl-2-oxothiazolidin-4-yl-carboxamide, Compound No. 1-83: (4R)-N-[(1S) -1-isobutyl-2-nitroxyethyl]-2-oxothiazolidin-4-yl-carboxamide, Compound No. 1-84: (4R)-N-[(1S)-1-isobutyl-2-nitroxyethyl]-5-methyl-2-oxothiazolidin-4-yl-carboxamide, Compound No. 1-87: (4R)-N-[(1S)-1-isobutyl-2-nitroxyethyl]-5-(4-methoxyphenyl)-2-oxothiazolidin-4-yl-carboxamide and Compound No. 1-90: (4R)-N-[(1S) -1-isobutyl-2-nitroxyethyl]-5-benzyl-2-oxothiazolidin-4-yl-carboxamide The preferred compounds of the general formula (II) can be specifically exemplified in Table 2 and Table 3. The compounds of Table 2 and Table 3 have the structural formulae of (II-1) and (II-2), respectively.

TABLE 2

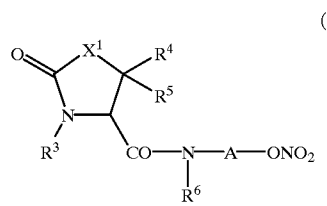

(II-1)

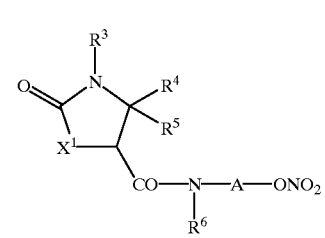

(II-2)

| Compound No | $R^3$ | $R^4$ | $R^5$ | $R^6$ | A | $X^1$ |
|---|---|---|---|---|---|---|
| 2-1 | H | H | H | H | $(CH_2)_2$ | S |
| 2-2 | Me | H | H | H | $(CH_2)_2$ | S |
| 2-3 | Et | H | H | H | $(CH_2)_2$ | S |
| 2-4 | $PhCH_2$ | H | H | H | $(CH_2)_2$ | S |
| 2-5 | H | Me | H | H | $(CH_2)_2$ | S |
| 2-6 | H | Et | H | H | $(CH_2)_2$ | S |
| 2-7 | H | Ph | H | H | $(CH_2)_2$ | S |
| 2-8 | H | 2-Thi | H | H | $(CH_2)_2$ | S |
| 2-9 | H | 3-Thi | H | H | $(CH_2)_2$ | S |
| 2-10 | H | 2-Fur | H | H | $(CH_2)_2$ | S |
| 2-11 | H | 3-Fur | H | H | $(CH_2)_2$ | S |
| 2-12 | H | $3-NO_2$-Ph | H | H | $(CH_2)_2$ | S |
| 2-13 | H | 4-Cl-Ph | H | H | $(CH_2)_2$ | S |
| 2-14 | H | 4-MeO-Ph | H | H | $(CH_2)_2$ | S |
| 2-15 | H | 4-Thiz | H | H | $(CH_2)_2$ | S |
| 2-16 | H | 3-Pyr | H | H | $(CH_2)_2$ | S |
| 2-17 | H | Me | Me | H | $(CH_2)_2$ | S |
| 2-18 | Me | Me | Me | H | $(CH_2)_2$ | S |
| 2-19 | Me | Me | Me | Me | $(CH_2)_2$ | S |
| 2-20 | Et | Ph | H | H | $(CH_2)_3$ | S |
| 2-21 | Et | Et | H | Me | $(CH_2)_4$ | S |
| 2-22 | $PhCH_2$ | Me | H | Et | $(CH_2)_2$ | S |
| 2-23 | $PhCH_2$ | Ph | H | Pr | $(CH_2)_4$ | S |
| 2-24 | Bu | H | H | H | $(CH_2)_2$ | S |
| 2-25 | H | 1-Naph | H | H | $(CH_2)_2$ | S |
| 2-26 | H | H | H | Me | $(CH_2)_2$ | S |
| 2-27 | H | H | H | $PhCH_2$ | $(CH_2)_2$ | S |
| 2-28 | H | $PhCH_2$ | H | H | $(CH_2)_2$ | S |
| 2-29 | $PhCH_2$ | H | H | H | $(CH_2)_3$ | S |
| 2-30 | H | H | H | H | $CH(Me)CH_2$ | S |
| 2-31 | H | H | H | H | $CH_2CH(Me)$ | S |
| 2-32 | H | H | H | H | $(CH_2)_5$ | S |
| 2-33 | H | H | H | H | $(CH_2)_6$ | S |
| 2-34 | H | H | H | H | $(CH_2)_2$ | O |
| 2-35 | Me | H | H | H | $(CH_2)_2$ | O |
| 2-36 | Et | H | H | H | $(CH_2)_2$ | O |
| 2-37 | $PhCH_2$ | H | H | H | $(CH_2)_2$ | O |
| 2-38 | H | Me | H | H | $(CH_2)_2$ | O |
| 2-39 | H | Et | H | H | $(CH_2)_2$ | O |
| 2-40 | H | Ph | H | H | $(CH_2)_2$ | O |
| 2-41 | H | 2-Thi | H | H | $(CH_2)_2$ | O |
| 2-42 | H | 3-Thi | H | H | $(CH_2)_2$ | O |
| 2-43 | H | 2-Fur | H | H | $(CH_2)_2$ | O |
| 2-44 | H | 3-Fur | H | H | $(CH_2)_2$ | O |
| 2-45 | H | $3-NO_2$-Ph | H | H | $(CH_2)_2$ | O |
| 2-46 | H | 4-Cl-Ph | H | H | $(CH_2)_2$ | O |
| 2-47 | H | 4-MeO-Ph | H | H | $(CH_2)_2$ | O |
| 2-48 | H | 4-Thiz | H | H | $(CH_2)_2$ | O |
| 2-49 | H | 3-Pyr | H | H | $(CH_2)_2$ | O |
| 2-50 | H | Me | Me | H | $(CH_2)_2$ | O |
| 2-51 | Me | Me | Me | H | $(CH_2)_2$ | O |
| 2-52 | Me | Me | Me | Me | $(CH_2)_2$ | O |
| 2-53 | Et | Ph | H | H | $(CH_2)_3$ | O |
| 2-54 | Et | Et | H | Me | $(CH_2)_4$ | O |
| 2-55 | $PhCH_2$ | Me | H | Et | $(CH_2)_2$ | O |
| 2-56 | $PhCH_2$ | Ph | H | Pr | $(CH_2)_4$ | O |
| 2-57 | Bu | H | H | H | $(CH_2)_2$ | O |
| 2-58 | H | 1-Naph | H | H | $(CH_2)_2$ | O |
| 2-59 | H | H | H | Me | $(CH_2)_2$ | O |
| 2-60 | H | H | H | $PhCH_2$ | $(CH_2)_2$ | O |

TABLE 2-continued (II-1)

$$\text{structure with } R^3, R^4, R^5, R^6, A, X^1, ONO_2$$

(II-2)

$$\text{structure with } R^3, R^4, R^5, R^6, A, X^1, ONO_2$$

| Compound No | R³ | R⁴ | R⁵ | R⁶ | A | X¹ |
|---|---|---|---|---|---|---|
| 2-61 | H | PhCH₂ | H | H | (CH₂)₂ | O |
| 2-62 | H | H | H | H | (CH₂)₃ | O |
| 2-63 | H | H | H | H | CH(Me)CH₂ | O |
| 2-64 | H | H | H | H | CH₂CH(Me) | O |
| 2-65 | H | H | H | H | (CH₂)₅ | O |
| 2-66 | H | H | H | H | (CH₂)₆ | O |
| 2-67 | H | H | H | H | (CH₂)₄ | S |
| 2-68 | H | H | H | H | (CH₂)₃ | S |
| 2-69 | H | 4-Me-CH₂Ph | H | H | (CH₂)₂ | S |
| 2-70 | H | 4-MeO—CH₂Ph | H | H | (CH₂)₂ | S |
| 2-71 | H | 4-F—CH₂Ph | H | H | (CH₂)₂ | S |
| 2-72 | H | 4-Cl—CH₂Ph | H | H | (CH₂)₂ | S |
| 2-73 | H | 4-OH—CH₂Ph | H | H | (CH₂)₂ | S |
| 2-74 | H | 4-Me-Ph | H | H | (CH₂)₂ | S |
| 2-75 | H | 4-F-Ph | H | H | (CH₂)₂ | S |
| 2-76 | H | 4-OH-Ph | H | H | (CH₂)₂ | S |
| 2-77 | H | 4-Me-CH₂Ph | H | H | (CH₂)₂ | O |
| 2-78 | H | 4-MeO—CH₂Ph | H | H | (CH₂)₂ | O |
| 2-79 | H | 4-F—CH₂Ph | H | H | (CH₂)₂ | O |
| 2-80 | H | 4-Cl—CH₂Ph | H | H | (CH₂)₂ | O |
| 2-81 | H | 4-OH—CH₂Ph | H | H | (CH₂)₂ | O |
| 2-82 | H | 4-Me-Ph | H | H | (CH₂)₂ | O |
| 2-83 | H | 4-F-Ph | H | H | (CH₂)₂ | O |
| 2-84 | H | 4-OH-Ph | H | H | (CH₂)₂ | O |
| 2-85 | H | H | H | H | (CH₂)₄ | O |
| 2-86 | H | Me | H | H | CH(Me)CH₂ | S |
| 2-87 | H | 3-Fur | H | H | CH(Me)CH₂ | S |
| 2-88 | H | 4-MeO-Ph | H | H | CH(Me)CH₂ | S |
| 2-89 | H | PhCH₂ | H | H | CH(Me)CH₂ | S |
| 2-90 | H | Me | H | H | CH(Me)CH₂ | O |
| 2-91 | H | 3-Fur | H | H | CH(Me)CH₂ | O |
| 2-92 | H | 4-MeO-Ph | H | H | CH(Me)CH₂ | O |
| 2-93 | H | PhCH₂ | H | H | CH(Me)CH₂ | O |

TABLE 3

| Compound No. | R³ | R⁴ | R⁵ | R⁶ | A | X¹ |
|---|---|---|---|---|---|---|
| 3-1 | H | H | H | H | (CH₂)₂ | S |
| 3-2 | Me | H | H | H | (CH₂)₂ | S |
| 3-3 | Et | H | H | H | (CH₂)₂ | S |
| 3-4 | PhCH₂ | H | H | H | (CH₂)₂ | S |
| 3-5 | H | Me | H | H | (CH₂)₂ | S |
| 3-6 | H | Et | H | H | (CH₂)₂ | S |
| 3-7 | H | Ph | H | H | (CH₂)₂ | S |
| 3-8 | H | 2-Thi | H | H | (CH₂)₂ | S |
| 3-9 | H | 3-Thi | H | H | (CH₂)₂ | S |
| 3-10 | H | 2-Fur | H | H | (CH₂)₂ | S |
| 3-11 | H | 3-Fur | H | H | (CH₂)₂ | S |
| 3-12 | H | 3-NO₂-Ph | H | H | (CH₂)₂ | S |
| 3-13 | H | 4-Cl-Ph | H | H | (CH₂)₂ | S |
| 3-14 | H | 4-MeO-Ph | H | H | (CH₂)₂ | S |
| 3-15 | H | 4-Thiz | H | H | (CH₂)₂ | S |
| 3-16 | H | 3-Pyr | H | H | (CH₂)₂ | S |
| 3-17 | H | Me | Me | H | (CH₂)₂ | S |
| 3-18 | Me | Me | Me | H | (CH₂)₂ | S |
| 3-19 | Me | Me | Me | Me | (CH₂)₂ | S |
| 3-20 | Et | Ph | H | H | (CH₂)₂ | S |
| 3-21 | Et | Et | H | Me | (CH₂)₄ | S |
| 3-22 | PhCH₂ | Me | H | Et | (CH₂)₂ | S |
| 3-23 | PhCH₂ | Ph | H | Pr | (CH₂)₄ | S |
| 3-24 | Bu | H | H | H | (CH₂)₂ | S |
| 3-25 | H | 1-Naph | H | H | (CH₂)₂ | S |
| 3-26 | H | H | H | Me | (CH₂)₂ | S |
| 3-27 | H | H | H | PhCH₂ | (CH₂)₂ | S |
| 3-28 | H | PhCH₂ | H | H | (CH₂)₂ | S |
| 3-29 | H | H | H | H | (CH₂)₃ | S |
| 3-30 | H | H | H | H | CH(Me)CH₂ | S |
| 3-31 | H | H | H | H | CH₂CH(Me) | S |
| 3-32 | H | H | H | H | (CH₂)₅ | S |
| 3-33 | H | H | H | H | (CH₂)₆ | S |
| 3-34 | H | H | H | H | (CH₂)₂ | O |
| 3-35 | Me | H | H | H | (CH₂)₂ | O |
| 3-36 | Et | H | H | H | (CH₂)₂ | O |
| 3-37 | PhCH₂ | H | H | H | (CH₂)₂ | O |
| 3-38 | H | Me | H | H | (CH₂)₂ | O |
| 3-39 | H | Et | H | H | (CH₂)₂ | O |
| 3-40 | H | Ph | H | H | (CH₂)₂ | O |
| 3-41 | H | 2-Thi | H | H | (CH₂)₂ | O |
| 3-42 | H | 3-Thi | H | H | (CH₂)₂ | O |
| 3-43 | H | 2-Fur | H | H | (CH₂)₂ | O |
| 3-44 | H | 3-Fur | H | H | (CH₂)₂ | O |
| 3-45 | H | 3-NO₂-Ph | H | H | (CH₂)₂ | O |
| 3-46 | H | 4-Cl-Ph | H | H | (CH₂)₂ | O |
| 3-47 | H | 4-MeO-Ph | H | H | (CH₂)₂ | O |
| 3-48 | H | 4-Thiz | H | H | (CH₂)₂ | O |
| 3-49 | H | 3-Pyr | H | H | (CH₂)₂ | O |
| 3-50 | H | Me | Me | H | (CH₂)₂ | O |
| 3-51 | Me | Me | Me | H | (CH₂)₂ | O |
| 3-52 | Me | Me | Me | Me | (CH₂)₂ | O |
| 3-53 | Et | Ph | H | H | (CH₂)₃ | O |
| 3-54 | Et | Et | H | Me | (CH₂)₄ | O |
| 3-55 | PhCH₂ | Me | H | Et | (CH₂)₂ | O |
| 3-56 | PhCH₂ | Ph | H | Pr | (CH₂)₄ | O |
| 3-57 | Bu | H | H | H | (CH₂)₂ | O |
| 3-58 | H | 1-Naph | H | H | (CH₂)₂ | O |
| 3-59 | H | H | H | Me | (CH₂)₂ | O |
| 3-60 | H | H | H | PhCH₂ | (CH₂)₂ | O |
| 3-61 | H | PhCH₂ | H | H | (CH₂)₂ | O |
| 3-62 | H | H | H | H | (CH₂)₃ | O |
| 3-63 | H | H | H | H | CH(Me)CH₂ | O |
| 3-64 | H | H | H | H | CH₂CH(Me) | O |
| 3-65 | H | 4-Me-Ph | H | H | (CH₂)₂ | O |
| 3-66 | H | 4-Me-Ph | H | H | (CH₂)₂ | S |
| 3-67 | H | 4-Me-CH₂Ph | H | H | (CH₂)₂ | S |
| 3-68 | H | 4-MeO-CH₂Ph | H | H | (CH₂)₂ | S |
| 3-69 | H | 4-F-CH₂Ph | H | H | (CH₂)₂ | S |
| 3-70 | H | 4-Cl-CH₂Ph | H | H | (CH₂)₂ | S |
| 3-71 | H | 4-OH-CH₂Ph | H | H | (CH₂)₂ | S |
| 3-72 | H | 4-F-Ph | H | H | (CH₂)₂ | S |
| 3-73 | H | 4-OH-Ph | H | H | (CH₂)₂ | S |
| 3-74 | H | 4-Me-CH₂Ph | H | H | (CH₂)₂ | O |
| 3-75 | H | 4-MeO-CH₂Ph | H | H | (CH₂)₂ | O |
| 3-76 | H | 4-F-CH₂Ph | H | H | (CH₂)₂ | O |
| 3-77 | H | 4-Cl-CH₂Ph | H | H | (CH₂)₂ | O |
| 3-78 | H | 4-OH-CH₂Ph | H | H | (CH₂)₂ | O |
| 3-79 | H | 4-F-Ph | H | H | (CH₂)₂ | O |
| 3-80 | H | 4-OH-Ph | H | H | (CH₂)₂ | O |
| 3-81 | H | H | H | H | (CH₂)₄ | S |
| 3-82 | H | H | H | H | (CH₂)₄ | O |
| 3-83 | H | Me | H | H | CH(Me)CH₂ | S |
| 3-84 | H | 3-Fur | H | H | CH(Me)CH₂ | S |
| 3-85 | H | 4-MeO-Ph | H | H | CH(Me)CH₂ | S |
| 3-86 | H | PhCH₂ | H | H | CH(Me)CH₂ | S |

TABLE 3-continued

| Compound No. | R³ | R⁴ | R⁵ | R⁶ | A | X¹ |
|---|---|---|---|---|---|---|
| 3-87 | H | Me | H | H | CH(Me)CH₂ | O |
| 3-88 | H | 3-Fur | H | H | CH(Me)CH₂ | O |
| 3-89 | H | 4-MeO-Ph | H | H | CH(Me)CH₂ | O |
| 3-90 | H | PhCH₂ | H | H | CH(Me)CH₂ | O |

In the above Tables 2 and 3, the abbreviation indicates the following group.

| Bu | Butyl |
|---|---|
| Et | Ethyl |
| Fur | Furyl |
| Me | Methyl |
| Naph | Naphthyl |
| Ph | Phenyl |
| Pr | Propyl |
| Prd | Pyridyl |
| Thi | Thienyl |
| Thiz | Thiazolyl |

In the above Tables, preferred are compounds of Compound Nos. 2-1, 2-2, 2-5, 2-7, 2-8, 2-9, 2-10, 2-11, 2-12, 2-13, 2-14, 2-16, 2-17, 2-25, 2-26, 2-28, 2-30, 2-31, 2-34, 2-35, 2-38, 2-40, 2-41, 2-42, 2-43, 2-44, 2-47, 2-61, 2-63, 2-67, 2-68, 2-69, 2-70, 2-71, 2-72, 2-73, 2-74, 2-75, 2-76, 2-77, 2-78, 2-79, 2-80, 2-81, 2-82, 2-83, 2-84, 2-85, 2-86, 2-87, 2-88, 2-89, 2-90, 2-91, 2-92, 2-93, 3-1, 3-5, 3-7, 3-14, 3-30, 3-34, 3-38, 3-40, 3-47, 3-65, 3-66, 3-67, 3-68, 3-69, 3-70, 3-71, 3-72, 3-73, 3-83, 3-84, 3-85, 3-86, 3-87, 3-88, 3-89 and 3-90;

more preferred are compounds of Compound Nos. 2-1, 2-2, 2-5, 2-7, 2-8, 2-14, 2-25, 2-28, 2-30, 2-34, 2-38, 2-41, 2-44, 2-47, 2-61, 2-63, 2-69, 2-70, 2-74, 2-78, 2-86, 2-88, 2-89, 2-90, 2-91, 2-92, 2-93, 3-1, 3-7, 3-14, 3-30, 3-66, 3-67, 3-68 and 3-85; and particularly preferred are the compounds of Compound No. 2-1: N-(2-nitroxyethyl)-2-oxothiazolidin-4-yl-carboxamide, Compound No. 2-5: N-(2-nitroxyethyl)-5-methyl-2-oxothiazolidin-4-yl-carboxamide, Compound No. 2-14: N-(2-nitroxyethyl)-5-(4-methoxyphenyl)-2-oxothiazolidin-4-yl-carboxamide, Compound No. 2-28: N-(2-nitroxyethyl)-5-benzyl-2-oxothiazolidin-4-yl-carboxamide, Compound No. 2-30: N-(1-methyl-2-nitroxyethyl)-2-oxothiazolidin-4-yl-carboxamide, Compound No. 2-34: N-(2-nitroxyethyl)-2-oxoxazolidin-4-yl-carboxamide, Compound No. 2-44: N-(2-nitroxyethyl)-5-(3-furyl)-2-oxoxazolidin-4-yl-carboxamide, Compound No. 2-61: N-(2-nitroxyethyl)-5-benzyl-2-oxoxazolidin-4-yl-carboxamide, Compound No. 2-63: N-(1-methyl-2-nitroxyethyl)-2-oxoxazolidin-4-yl-carboxamide, Compound No. 2-86: N-(1-methyl-2-nitroxyethyl)-5-methyl-2-oxothiazolidin-4-yl-carboxamide, Compound No. 2-88: N-(1-methyl-2-nitroxyethyl)-5-(4-methoxyphenyl)-2-oxothiazolidin-4-yl-carboxamide, Compound No. 2-89: N-(1-methyl-2-nitroxyethyl)-5-benzyl-2-oxothiazolidin-4-yl-carboxamide, Compound No. 2-91: N-(1-methyl-2-nitroxyethyl)-5-(3-furyl)-2-oxoxazolidin-4-yl-carboxamide, Compound No. 2-93: N-(1-methyl-2-nitroxyethyl)-5-benzyl-2-oxoxazolidin-4-yl-carboxamide, Compound No. 3-1: N-(2-nitroxyethyl)-2-oxothiazolidin-5-yl-carboxamide, Compound No. 3-14: N-(2-nitroxyethyl)-4-(4-methoxyphenyl)-2-oxothiazolidin-5-yl-carboxamide, Compound No. 3-30: N-(1-methyl-2-nitroxyethyl)-2-oxothiazolidin-5-yl-carboxamide and Compound No. 3-85: N-(1-methyl-2-nitroxyethyl)-4-(4-methoxyphenyl)-2-oxothiazolidin-5-yl-carboxamide.

The compound of the present invention having the general formula (I) is easily prepared according to the following methods.

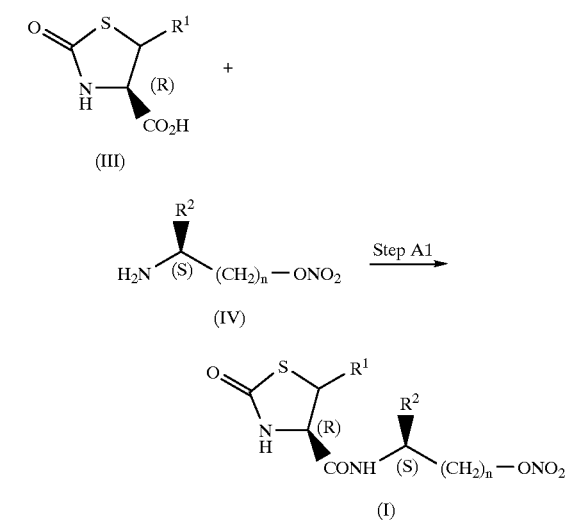

Method A

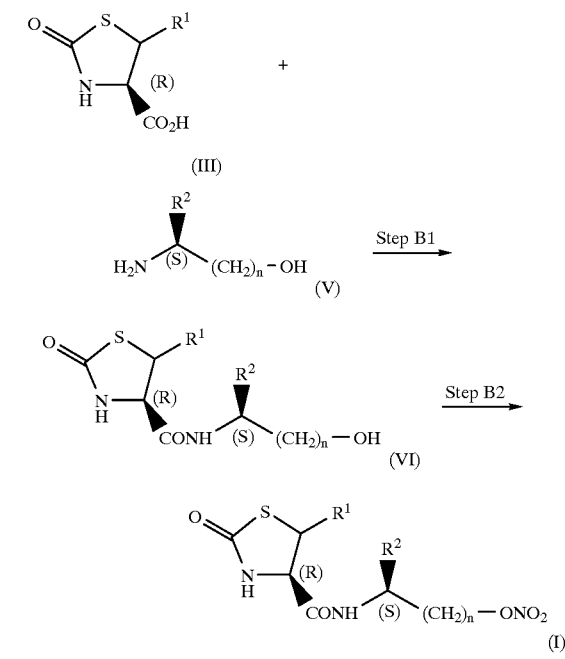

Method B

-continued

Method C

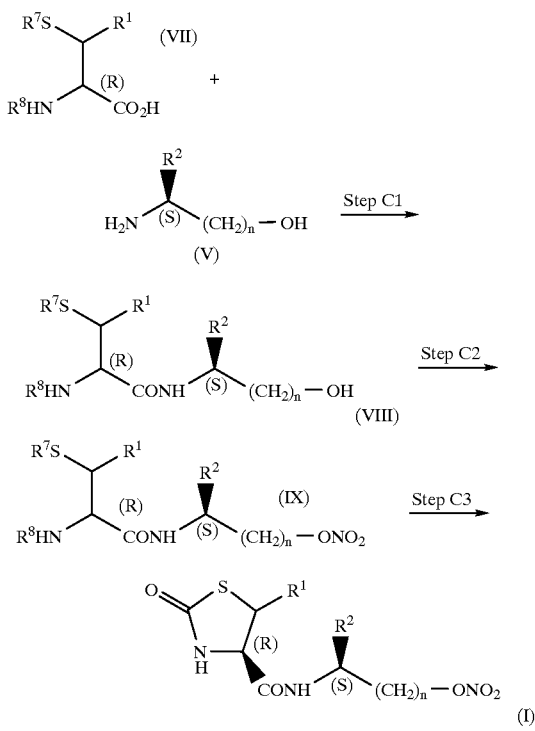

In the above formulae, $R^1$, $R^2$ and n have the same meanings as defined above, $R^7$ represents a protective group of a mercapto group and $R^8$ represents a protective group of an amino group.

The protective group of the mercapto group is not particularly limited so long as it is well known in the field of synthetic organic chemistry and includes preferably a tri-substituted silyl group having a substituent selected from the group consisting of a $C_1$–$C_4$ alkyl group, a phenyl group and a phenyl group substituted with $C_1$–$C_4$ alkyl, $C_1$–$C_4$ alkoxy or halogen, a benzyl group, a benzyl group substituted with $C_1$–$C_4$ alkyl, $C_1$–$C_4$ alkoxy or halogen, a benzyloxycarbonyl group, a benzyloxycarbonyl group substituted with $C_1$–$C_4$ alkyl, $C_1$–$C_4$ alkoxy or halogen, a t-butyl group or a t-butoxycarbonyl group, more preferably a trimethylsilyl group, a triethylsilyl group, a t-butyldimethylsilyl group, a phenyldimethylsilyl group, a methoxybenzyl group, a dimethoxybenzyl group, a methoxybenzyloxycarbonyl group, a dimethoxybenzyloxycarbonyl group or a t-butoxycarbonyl group, still more preferably a t-butyldimethylsilyl group, a 4-methoxybenzyl group, a 4-methoxybenzyloxycarbonyl group or a t-butoxycarbonyl group, and particularly preferably a t-butoxycarbonyl group.

The protective group of the amino group is not particularly limited so long as it is well known in the field of synthetic organic chemistry and includes preferably a tri-substituted silyl group having a substituent selected from the group consisting of a $C_1$–$C_4$ alkyl group, a phenyl group and a phenyl group substituted with $C_1$–$C_4$ alkyl, $C_1$–$C_4$ alkoxy or halogen, a benzyl group, a benzyl group substituted with $C_1$–$C_4$ alkyl, $C_1$–$C_4$ alkoxy or halogen, a benzyloxycarbonyl group, a benzyloxycarbonyl group substituted with $C_1$–$C_4$ alkyl, $C_1$–$C_4$ alkoxy or halogen, a t-butyl group or a t-butoxycarbonyl group, more preferably a trimethylsilyl group, a triethylsilyl group, a t-butyldimethylsilyl group, a phenyldimethylsilyl group, a methoxybenzyl group, a dimethoxybenzyl group, a methoxybenzyloxycarbonyl group, a dimethoxybenzyloxycarbonyl group or a t-butoxycarbonyl group, still more preferably a t-butyldimethylsilyl group, a 4-methoxybenzyl group, a 4-methoxybenzyloxycarbonyl group or a t-butoxycarbonyl group, and particularly preferably a t-butoxycarbonyl group.

Method A is a method for preparing the compound (I).

Step A1 is to prepare a compound having the general formula (I) and is carried out by reacting a compound having the general formula (III) or a reactive derivative thereof (acid halides, mixed acid anhydrides or active esters) with a compound having the general formula (IV) or its acid addition salt (for example, mineral acid salts such as hydrochlorides, nitrates and sulfates) in an inert solvent, and is carried out, for example, by an acid halide method, a mixed acid anhydride method, an active ester method or a condensation method.

The acid halide method is carried out by reacting the compound (III) with a halogenating agent (for example, thionyl chloride, oxalyl chloride, phosphorus pentachloride, etc.) in an inert solvent to prepare the acid halide, and by reacting the acid halide with the compound (IV) or an acid addition salt thereof in an inert solvent in the presence or absence of a base.

The base employable here may include, for example, organic amines such as triethylamine, N-methylmorpholine, pyridine and 4-dimethylaminopyridine; alkali metal hydrogencarbonates such as sodium hydrogencarbonate and potassium hydrogencarbonate; and alkali metal carbonates such as sodium carbonate and potassium carbonate, and preferably organic amines.

The inert solvent employable here is not particularly limited so long as it does not affect the reaction and may include, for example, hydrocarbons such as hexane, cyclohexane, benzene, toluene and xylene; halogenated hydrocarbons such as dichloromethane, 1,2-dichloroethane and carbon tetrachloride; ethers such as ether, tetrahydrofuran and dioxane; ketones such as acetone; amides such as N,N-dimethylformamide, N,N-dimethylacetamide, N-methyl-2-pyrrolidone and hexamethylphosphoramide; and sulfoxides such as dimethyl sulfoxide, and preferably hydrocarbons, halogenated hydrocarbons, ethers or amides.

The reaction temperature varies depending on the starting compounds (III) and (IV), the kind of solvent etc., and the reaction temperatures for both the reaction of the halogenating agent with the compound (III) and the reaction of the acid halide with the compound (IV) are usually $-20°$ C. to $150°$ C. Preferably, the reaction temperature for the former reaction is $-10°$ C. to $50°$ C., and for the latter reaction is $0°$ C. to $100°$ C. The reaction time varies depending on the reaction temperature etc., and the reaction time of both reactions is usually 15 minutes to 24 hours (preferably 30 minutes to 16 hours).

The mixed acid anhydride method is carried out by reacting a $C_1$–$C_6$ alkyl halogenocarbonate, a di-$C_1$–$C_6$ alkylcyanophosphoric acid or a di-$C_6$–$C_{10}$ arylphosphoryl azide with the compound (III) to prepare the mixed acid anhydride and by reacting the resulting mixed acid anhydride with the compound (IV) or its acid addition salt.

The reaction for preparing the mixed acid anhydride is carried out by reacting a $C_1$–$C_6$ alkyl halogenocarbonate such as methyl chlorocarbonate, ethyl chlorocarbonate, isobutyl chlorocarbonate and hexyl chlorocarbonate (preferably ethyl chlorocarbonate or isobutyl chlorocarbonate), a di-$C_1$–$C_6$ alkylcyanophosphoric acid such as dimethylcyanophosphoric acid, diethylcyanophosphoric acid and dihexylcyanophosphoric acid (preferably diethylcyanophosphoric acid) or a di-$C_6$–$C_{10}$ arylphosphoryl azide such as diphenylphosphoryl azide, di(p-nitrophenyl)phosphoryl azide and dinaphthylphosphoryl azide (preferably diphenylphosphoryl azide) with the compound (III), preferably in an inert solvent in the presence of a base.

The base and the inert solvent employable here are similar to those employable in the acid halide method.

The reaction temperature varies depending on the starting compound (III), the kind of solvent, etc., and is usually –20° C. to 50° C. (preferably 0° C. to 30° C.). The reaction time varies depending on the reaction temperature etc. and is usually 15 minutes to 24 hours (preferably 30 minutes to 16 hours).

The reaction of the mixed acid anhydride with the compound (IV) or its acid addition salt is preferably carried out in an inert solvent in the presence or absence of a base. The base and the inert solvent employable here are similar to those employable in the acid halide method.

The reaction temperature varies depending on the starting compound (IV), the kind of solvent, etc., and is usually –20° C. to 100° C. (preferably –10° C. to 50° C). The reaction time varies depending on the reaction temperature etc., and is usually 15 minutes to 24 hours (preferably 30 minutes to 16 hours).

In the case where dialkylcyanophosphoric acid or diarylphosphoryl azide is used, the present method can be carried out by reacting the compound (III) with the compound (IV) directly in the presence of a base.

The active ester method can be carried out by reacting the compound (III) with an active esterifying agent (for example, an N-hydroxy compound such as N-hydroxysuccinimide and N-hydroxybenzotriazole and the like) in the presence of a condensation agent (for example, dicyclohexylcarbodiimide, carbonyldiimidazole and the like) to prepare the active ester, and by reacting the active ester with the compound (IV) or its acid addition salt.

The reaction for preparing the active ester is preferably carried out in an inert solvent, and the inert solvent employable here is similar to that employable in the acid halide method.

The reaction temperature varies depending on the starting compounds (III) and (IV), the kind of solvent, etc., the reaction temperature for the active esterification reaction is usually –20° C. to 50° C. (preferably –10° C. to 30° C.), and the reaction temperature for the reaction of the active ester compound with the compound (IV) is usually –20° C. to 50° C. (preferably –10° C. to 30° C.). The reaction time varies depending on the reaction temperature etc., and the reaction times for both reactions are usually 15 minutes to 24 hours (preferably 30 minutes to 16 hours).

The condensation method can be carried out by reacting, the compound (III) with the compound (IV) or an acid addition salt thereof directly in the presence of a condensation agent (for example, dicyclohexylcarbodiimide, carbonyldiimidazole, 1-(N,N-dimethylaminopropyl)-3-ethylcarbodiimide hydrochloride and the like). The present reaction is carried out in the similar manner to the reaction for preparing the active ester.

After completion of the reaction, the desired compound in each reaction is collected from the reaction mixture by conventional procedures. For example, the desired compound of each reaction can be obtained by appropriately separating the insolubles by filtration and collecting the precipitated crystal by filtration; or by appropriately separating the insolubles by filtration, appropriately neutralizing, distilling off the solvent, adding water to the reaction mixture, extracting the mixture with a water-immiscible organic solvent such as ethyl acetate, drying the organic layer and evaporating the extracting solvent. If necessary, the compound thus obtained can be further purified by conventional procedures, for example, recrystallization, column chromatography and the like.

The starting compound (III) of Method A is known or is easily prepared according to known methods or methods which are similar thereto [for example, Tetrahedron, 45, 7459 (1989), J. Am. Chem. Soc., 79, 5203 (1957), J. Am. Chem. Soc., 111, 6354 (1989), etc.].

Method B is another method for preparing the compound (I).

Step B1 is to prepare a compound having the general formula (VI) and is carried out by reacting the compound (III) or a reactive derivative thereof with a compound having the general formula (V) in an inert solvent. The present step is carried out, for example, by the acid halide method, the mixed acid anhydride method, the active ester method or the condensation method, and is carried out in the same manner as in Step A1.

Step B2 is to prepare a compound having the general formula (I) and is carried out by reacting the compound having the general formula (VI) with a nitrating agent in the absence or presence of an inert solvent.

The nitrating agent employable here may include, for example, fuming nitric acid, nitrocollidium tetrafluoroboron, thionylchloride nitric acid, thionylnitric acid and nitronium tetrafluoroboron, and preferably fuming nitric acid, nitrocollidium tetrafluoroboron or thionylchloride nitric acid.

The inert solvent employable here is not particularly limited so long as it does not affect the reaction and may include, for example, hydrocarbons such as hexane, cyclohexane, benzene, toluene and xylene; halogenated hydrocarbons such as dichloromethane, 1,2-dichloroethane and carbon tetrachloride; ethers such as ether, tetrahydrofuran and dioxane; ketones such as acetone; nitrites such as acetonitrile; amides such as N,N-dimethylformamide, N,N-dimethylacetamide, N-methyl-2-pyrrolidone and hexamethylphosphoramide; and sulfoxides such as dimethyl sulfoxide, preferably halogenated hydrocarbons, ethers or nitrites, and particularly preferably nitriles.

The reaction temperature varies depending on the starting compound (VI), the kind of nitrating agent, etc. and is usually –20° C. to 50° C., and preferably about room temperature. The reaction time varies depending on the reaction temperature etc., and is usually 30 minutes to 24 hours (preferably 1 hour to 10 hours).

The compound (I) is also prepared by reacting the compound (VI) with a sulfonylating agent (for example, $C_1$–$C_4$ alkanesulfonyl halides such as methanesulfonyl chloride, methanesulfonyl bromide, ethanesulfonyl chloride and butanesulfonyl chloride; $C_6$–$C_{10}$ aryl halides such as benzenesulfonyl chloride, p-toluenesulfonyl chloride, p-toluenesulfonyl bromide and naphthylsulfonyl chloride; or $C_1$–$C_4$ alkanesulfonic anhydrides such as methanesulfonic anhydride, ethanesulfonic anhydride and butanesulfonic anhydride, preferably methanesulfonyl chloride, ethanesulfonyl chloride, benzenesulfonyl chloride, p-toluenesulfonyl chloride or methanesulfonic anhydride, and particularly preferably methanesulfonyl chloride) at –20° C. to 50° C. (preferably about room temperature) for 30 minutes to 24 hours (preferably 1 hour to 10 hours) in an inert solvent (for example, hydrocarbons such as hexane, cyclohexane, benzene, toluene and xylene; halogenated hydrocarbons such as dichloromethane, 1,2-dichloroethane and carbon tetrachloride; or ethers such as ether, tetrahydrofuran and dioxane; or nitriles such as acetonitrile, preferably nitriles, and particularly preferably acetonitrile) in the presence or absence of a base (for example, organic amines such as triethylamine, N-methylmorpholine, pyridine and 4-dimethylaminopyridine, and preferably triethylamine) to prepare the sulfonyloxy compound, and then by reacting the sulfonyloxy compound with tetra ($C_1$–$C_4$ alkyl)ammonium nitrate (for example, tetramethylammonium nitrate, tetraethylammonium nitrate or tetrabutylammonium nitrate, and preferably tetrabutylammonium nitrate) at 0° C. to 200° C. (preferably 50° C. to 150° C.) for 30 minutes to 24 hours (preferably 1 hour to 10 hours) in an inert solvent (for example, aromatic hydrocarbons such as benzene, toluene and xylene, and preferably toluene).

After completion of the reaction, the desired compound of each reaction is collected from the reaction mixture according to conventional procedures. For example, the desired compound can be obtained by collecting the precipitated crystal by filtration; by distilling off the solvent; or by appropriately distilling off the solvent, adding water to the reaction mixture, extracting the mixture with a water-immiscible organic solvent such as ethyl acetate, drying the organic layer and evaporating the extracting solvent. If necessary, the compound thus obtained can be further purified by conventional procedures, for example, recrystallization, column chromatography and the like.

Method C is another method for preparing the compound (I).

Step C1 is to prepare a compound having the general formula (VIII) and is carried out by reacting a compound having the general formula (VII) or a reactive derivative thereof with the compound (V) in an inert solvent. The present step can be carried out, for example, by the acid halide method, the mixed acid anhydride method, the active ester method or the condensation method and is carried out in the same manner as in Step A1 of the above Method A.

Step C2 is to prepare a compound having the general formula (IX) and is carried out by reacting a compound having the general formula (VIII) with a nitrating agent in the absence or presence of an inert solvent. The present step is carried out in the same manner as in Step B2 of the above Method B.

Step C3 is to prepare the compound (I) and is carried out by eliminating the protective group of the mercapto group and the protective group of the amino group of the compound (IX) and then reacting the resulting compound with carbonyl compounds such as carbonyldiimidazole; phosgene derivatives such as phosgene and triphosgene; $C_1$–$C_4$ alkyl halogenocarbonates such as methyl chlorocarbonate, ethyl chlorocarbonate, ethyl bromocarbonate, propyl chlorocarbonate and butyl chlorocarbonate; and phenyl halogenocarbonate derivatives such as phenyl chlorocarbonate, phenyl bromocarbonate, tolyl chlorocarbonate, methoxyphenyl chlorocarbonate and chlorophenyl chlorocarbonate (preferably carbonyldiimidazole, phosgene, triphosgene, methyl chlorocarbonate, ethyl chlorocarbonate, ethyl bromocarbonate or phenyl chlorocarbonate, and particularly preferably carbonyldiimidazole).

The reaction for eliminating the protective group of the mercapto group and the protective group of the amino group is carried out by the method well known in the field of synthetic organic chemistry. For example, the protective group of the mercapto group and the protective group of the amino group are eliminated by reacting a corresponding compound with an acid in an inert solvent.

The acid employable here may include, for example, mineral acis such as hydrochloric acid, nitric acid and sulfuric acid; carboxylic acis such as acetic acid and trifluoroacetic acid; and sulfonic acids such as methanesulfonic acid, benzenesulfonic acid and p-toluenesulfonic acid, preferably hydrochloric acid, trifluoroacetic acid or p-toluenesulfonic acid, and particularly preferably hydrochloric acid.

The inert solvent employable here is not particularly limited so long as it does not affect the reaction and may include, for example, hydrocarbons such as hexane, cyclohexane, benzene, toluene and xylene; halogenated hydrocarbons such as dichloromethane, 1,2-dichloroethane and carbon tetrachloride; ethers such as ether, tetrahydrofuran and dioxane; ketones such as acetone; and nitriles such as acetonitrile, preferably halogenated hydrocarbons or ethers, and particularly preferably ethers.

The reaction temperature varies depending on the starting compound etc., and is usually −20° C. to 50° C., and preferably about room temperature. The reaction time varies depending on the reaction temperature etc., and is usually 30 minutes to 24 hours (preferably 1 hour to 10 hours).

In the case where the protective group of the mercapto group and/or the protective group of the amino group are a tri-substituted silyl group, the protective group is also eliminated by reacting the corresponding compound with a reagent producing a fluoro anion such as tetrabutylammonium fluoride and potassium fluoride instead of the acid.

The protective group of the mercapto group and the protective group of the amino group may be eliminated in order, and are preferably eliminated at the same time under the same condition.

The reaction of the compound obtained by eliminating the protective group of the mercapto group and the protective group of the amino group with the carbonyl compound is preferably carried out in an inert solvent.

The inert solvent employable here is not particularly limited so long as it does not affect the reaction and may include, for example, hydrocarbons such as hexane, cyclohexane, benzene, toluene and xylene; halogenated hydrocarbons such as dichloromethane, 1,2-dichloroethane and carbon tetrachloride; ethers such as ether, tetrahydrofuran and dioxane; ketones such as acetone; and nitriles such as acetonitrile, preferably halogenated hydrocarbons or ethers, and particularly preferably halogenated hydrocarbons.

The reaction temperature varies depending on the starting compound etc., and is usually −20° C. to 50° C., and preferably about room temperature. The reaction time varies depending on the reaction temperature etc., and is usually 10 minutes to 10 hours (preferably 20 minutes to 5 hours).

After completion of the reaction, the desired compound of each reaction is collected from the reaction mixture by conventional procedures. For example, the desired compound can be obtained by distilling off the solvent; or by appropriately distilling off the solvent, adding water to the reaction mixture, extracting the mixture with a water-immiscible organic solvent such as ethyl acetate, drying the organic layer and evaporating the extracting solvent. If necessary, the compound thus obtained can be further purified by conventional procedures, for example, recrystallization, column chromatography and the like.

The starting compound (VII) of Method C is known or is easily prepared according to known methods or methods which are similar thereto [for example, Chem. Absts., 74, 100379b (1971)].

A compound having the general formula (I') also has an excellent anti-ulcerative action and is prepared in the same manner as in the above process using a compound having the general formula (IV') instead of the compound (IV) or a compound having the general formula (V') instead of the compound (V).

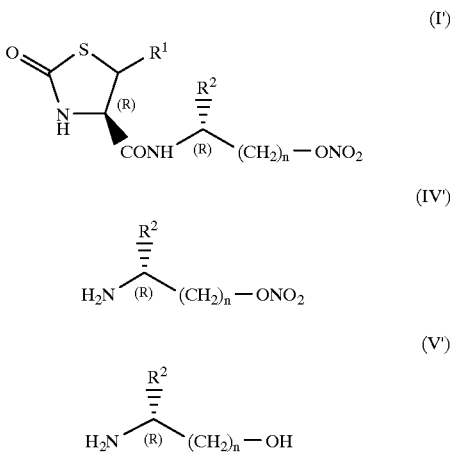

In the above formulae, $R^1$, $R^2$ and n have the same meanings as defined above.

The compound having the general formula (II) which is an active ingredient of a preventive agent or a therapeutic agent for an ulcerative disease of the present invention is a known compound or is easily prepared according to conventional procedures (for example, Japanese Unexamined Patent Publication (KOKAI) No. Hei 5-213910 etc.).

EFFECT OF THE INVENTION

The compound having the above general formula (I) of the present invention exhibits a potent collateral vessel dilating action, a weak toxicity and less side effects such as headache, dizziness, tachycardia or detrimental effects on the digestive system, liver, bone etc., and it does not undergo the first-pass effect, and it is useful as a preventive agent and a therapeutic agent (preferably a therapeutic agent) for angina pectoris.

Meanwhile, the compound having the above general formula (II) or a pharmacologically acceptable salt thereof exhibits a potent anti-ulcerative action, a weak toxicity and less side effects such as headache, dizziness, tachycardia or detrimental effects on the digestive system, liver, bone etc., and it is useful as a preventive agent and a therapeutic agent (preferably a therapeutic agent) for an ulcerative disease.

The compound (I) has characteristics that its storage stability is excellent and it can be handled easily.

INDUSTRIAL APPLICABILITY

In the case where the compound (I) of the present invention is used as a therapeutic agent or a preventive agent for angina pectoris; or the compound (II) and a pharmacologically acceptable salt thereof are used as a preventive agent or a therapeutic agent for an ulcerative disease, it can be administered as such or as a mixture, for example, with a suitable pharmacologically acceptable excipient, diluent or the like in the form of a tablet, a capsule, a granule, a powder, a syrup for oral administration and an injection preparation for parenteral administration.

These preparations are prepared by the known method using additives such as excipients (for example, sugar derivatives such as lactose, sucrose, glucose, mannitol and sorbitol; starch derivatives such as corn starch, mashed potato starch, a-starch, dextrine and carboxymethyl starch; cellulose derivatives such as crystalline cellulose, low hydroxypropyl-substituted cellulose, hydroxypropylmethyl cellulose, carboxymethyl cellulose, carboxymethyl cellulose calcium and internally bridged carboxymethyl cellulose sodium; gum arabic; dextran; Pullulan; silicate derivatives such as light silicic acid anhydride, synthetic aluminum silicate and magnesium meta-silicic acid aluminate; phosphate derivatives such as calcium phosphate; carbonate derivatives such as calcium carbonate; and sulfate derivatives such as calcium sulfate), binders (for example, the above-mentioned excipients; gelatin; polyvinylpyrrolidone; and Macrogol); disintegrating agents (for example, the above-mentioned excipients; chemically modified starch, cellulose derivatives, etc. such as Crosscarmelose sodium, sodium carboxymethyl starch and bridged polyvinylpyrrolidone), lubricants (for example, talc; stearic acid; and metal stearates such as calcium stearate and magnesium stearate; colloidal silica; waxes such as beeswax and spermaceti; boric acid; glycol; carboxylic acids such as fumaric acid and adipic acid; sodium carboxylate such as sodium benzoate; sulfates such as sodium sulfate; leucine; lauryl sulfates such as sodium laurylsulfate and magnesium laurylsulfate; silicic acids such as silicic acid anhydride and silicic acid hydrate; and starch derivatives in the above excipients), stabilizers (for example, p-hydroxybenzoates such as methylparaben and propylparaben; alcohols such as chlorobutanol, benzyl alcohol and phenylethyl alcohol; benzalkonium chloride; phenols such as phenol and cresol; thimerosal; acetic anhydride; and sorbic acid); corrigents (for example, sweeteners, sour agents and perfumes conventionally used), diluents and solvents for injection agents (for example, water, ethanol and glycerin). The dose varies depending on the condition and age of the patient to be treated, and it is desirably administered 1 to 6 times daily depending on the condition: in the case of oral administration, the lower limit of 1 mg each time (preferably 5 mg) and the upper limit of 1000 mg (preferably 300 mg) for an adult; and in the case of intravenous administration, the lower limit of 0.1 mg each time (preferably 0.5 mg) and the upper limit of 100 mg (preferably 50 mg) for an adult.

BEST MODE FOR PRACTISING THE INVENTION

The present invention will be described below more specifically by showing Examples, Reference examples, Test examples and Preparation examples, but the invention is not limited thereto.

EXAMPLE 1

(4R)-N-[(1S)-1-Methyl-2-nitroxyethyl]-2-oxothiazolidin-4-yl-carboxamide (Exemplary Compound No. 1-1)

In 60 ml of dry tetrahydrofuran were suspended 2.06 g of (4R)-2-oxothiazolidine-4-carboxylic acid and 2.00 g of (1S)-1-methyl-2-nitroxyethylamine hydrochloride, 4.5 ml of triethylamine and 3.00 ml of diphenylphosphoryl azide were added thereto with stirring under ice-cooling, and the mixture was stirred at room temperature for 5 hours. Then, the solvent was distilled off under reduced pressure and the residue was purified by silica gel column chromatography employing cyclohexane-ethyl acetate (1:4) as an eluent to obtain 3.00 g of colorless crystals. The crystals were recrystallized from ethyl acetate to obtain 0.964 g of the desired compound as colorless needle crystals.

m.p.: 122–123° C. (decomp.) NMR spectrum (CDCl$_3$+ DMSO-d$_6$) δ ppm: 1.27(3H, d, J=6.6 Hz), 3.67(2H, d, J=6.6 Hz), 4.10–4.57(4H, m), 7.57(1H, bs), 7.78(1H, br.s)

EXAMPLE 2

(4R)-N-[(1S)-1-Methyl-2-nitroxyethyl]-2-oxothiazolidin-4-yl-carboxamide (Exemplary Compound No. 1-1)

(2a) (4R)-N-[(1S)-1-Methyl-2-hydroxyethyl]-2-oxothiazolidin-4-yl-carboxamide

In 20 ml of dry tetrahydrofuran were dissolved 1.0 g of (4R)-2-oxothiazolidine-4-carboxylic acid and 0.56 g of L-alaninol, 2.8 ml of triethylamine and 1.8 ml of diphenylphosphoryl azide were added thereto with stirring under ice-cooling, and the mixture was stirred at room temperature for 3 hours. Then, the solvent was distilled off under reduced pressure and the obtained residue was purified by silica gel column chromatography employing ethyl acetate as an eluent and further purified by silica gel column chromatography employing dichloromethane-methanol (95:5) as an eluent to obtain 0.92 g of the desired compound as colorless crystals.

m.p.: 160–162° C. NMR spectrum (DMSO-$d_6$) δ ppm: 1.04(3H, d, J=6.7 Hz), 3.20–3.40(3H, m), 3.63(1H, dd, J=8.6 Hz, J=11.2 Hz), 3.70–3.88(1H, m), 4.16–4.22(1H, m), 4.73 (1H, t, J=5.6 Hz), 7.83(1H, d, J=7.9 Hz), 8.24(1H, bs)

(2b) (4R)-N-[(1s)-1-Methyl-2-nitroxyethyl]-2-oxothiazolidin-4-yl-carboxamide

In 10 ml of dry acetonitrile were dissolved 478 mg of nitronium tetrafluoroboron (85% content), 0.43 ml of 2,4,6-collidine was added thereto with stirring under ice-cooling, and the mixture was stirred under ice-cooling for 30 minutes. To the resulting mixture were added 500 mg of (4R)-N-[(1S)-1-methyl-2-hydroxyethyll-2-oxothiazolidin-4-yl-carboxamide, and the mixture was stirred at room temperature for 1 hour and 45 minutes. Then, the solvent was distilled off under reduced pressure and the thus obtained residue was purified by silica gel column chromatography employing cyclohexane-ethyl acetate (3:7) as an eluent to obtain 178 mg of the desired compound as colorless crystals.

m.p.: 119–122° C. (decomp.) NMR spectrum of the compound was identical with that of the compound of Example 1.

EXAMPLE 3

(4R)-N-[(1S)-1-Methyl-2-nitroxyethyl]-2-oxothiazolidin-4-yl-carboxamide (Exemplary Compound No. 1-1)

(3a) N-[(1S)-1-Methyl-2-hvdroxyethyl]-(2R)-2-t-butoxycarbonylamino-3-t-butoxycarbonylthiopropanamide In 100 ml of dry tetrahydrofuran were dissolved 5.0 g of N,S-di-t-butoxycarbonyl-L-cysteine and 1.3 g of L-alaninol, 4.4 ml of triethylamine and 4.0 ml of diphenylphosphoryl azide were added thereto with stirring under ice-cooling, and the mixture was stirred at room temperature for 4 hours. Then, the solvent was distilled off under reduced pressure and the residue was purified by silica gel column chromatography employing cyclohexane-ethyl acetate (1:1) as an eluent to obtain 3.55 g of the desired compound as colorless crystals.

m.p.: 70–72° C. NMR spectrum (CDCl$_3$) δ ppm: 1.19(3H, d, J=6.9 Hz), 1.45(9H, s), 1.51(9H, s), 2.65–2.90(1H, bs), 3.03–3.30(2H, m), 3.42–3.58(1H, m), 3.63–3.78(1H, m), 3.95–4.04(1H, m), 4.20–4.35(1H, m), 5.42–5.68(1H, bm), 6.46(1H, d, J=7.8 Hz)

(3b) N-[(1S)-1-Methyl-2-nitroxyethyl]-(2R)-2-t-butoxycarbonylamino-3-t-butoxycarbonylthiopropanamide In 25 ml of dry acetonitrile were dissolved 1.24 g of nitronium tetrafluoroboron (85% content), 1.12 g of 2,4,6-collidine was added thereto with stirring under ice-cooling, and the mixture was stirred under ice-cooling for 30 minutes. Then, a solution obtained by dissolving 2.5 g of N-[(1S)-1-methyl-2-hydroxyethyl]-(2R)-2-t-butoxycarbonylamino-3-t-butoxycarbonylthiopropanamide in 25 ml of dry acetonitrile was added to the mixture and the resulting mixture was stirred at room temperature for 3 hours. Then, the solvent was distilled off under reduced pressure and the thus obtained residue was purified by silica gel column chromatography employing cyclohexane-ethyl acetate (4:1) as an eluent to obtain 1.39 g of the desired compound as pale yellow crystals.

m.p.: 123–124° C. (decomp.) NMR spectrum (CDCl$_3$) δ ppm: 1.27(3H, d, J=6.8 Hz), 1.45(9H, s), 1.51(9H, s), 3.05–3.28(2H, m), 4.20–4.55(4H, m), 5.42(1H, d, J=6.3 Hz), 6.45–6.65(1H, bs)

(3c) (4R)-N-[(1S)-1-Methyl-2-nitroxyethyl]-2-oxothiazolidin-4-yl-carboxamide

In 10 ml of a solution of 4N hydrochloric acid in dioxane were dissolved 1.0 g of N-(1S)-1-methyl-2-nitroxyethyl]-(2R)-2-t-butoxycarbonylamino-3-t-butoxycarbonylthiopropanamide, and the solution was stirred at room temperature for 2 hours. The solvent was distilled off under reduced pressure, benzene was added to the residue, and the solution was evaporated to dryness under reduced pressure. The thus obtained residue was suspended in 10 ml of dry dichloromethane, 0.46 g of carbodiimidazole were added thereto, and the mixture was stirred at room temperature for 40 minutes. The reaction mixture was purified by silica gel column chromatography employing ethyl acetate as an eluent to obtain 0.45 g of pale yellow crystals. The crystals were recrystallized from ethyl acetate to obtain 84 mg of the desired compound as colorless crystals.

m.p.: 125–126° C. (decomp.) NMR spectrum of the compound was identical with that of the compound of Example 1.

EXAMPLE 4

(4R)-N-[(1S)-1-Ethyl-2-nitroxyethyl]-2-oxothiazolidin-4-yl-carboxamide (Exemplary Compound No. 1-15)

In 10 ml of dry tetrahydrofuran were suspended 0.50 g of (4R)-2-oxothiazolidine-4-carboxylic acid and 0.70 g of (1S)-1-ethyl-2-nitroxyethylamine hydrochloride, 1.40 ml of triethylamine and 0.62 ml of diethylcyanophosphoric acid were added thereto, and the mixture was stirred at room temperature for 2 hours. The solvent was distilled off under reduced pressure and the residue was purified by silica gel column chromatography employing cyclohexane-ethyl acetate (1:2) as an eluent to obtain a pale yellow oil. Isopropyl ether was added to the oil to obtain a pale yellow powder. The powder was dissolved in 10 ml of acetone and further 5 ml of ethyl acetate was added thereto. The acetone was distilled off under reduced pressure and the mixture was left to stand at room temperature to obtain 0.24 g of the desired compound as colorless columnar crystals.

m.p.: 106–107° C. (decomp.) NMR spectrum (d$_6$-DMSO) δ ppm: 0.87(3H, t, J=7.4 Hz), 1.30–1.68(2H, m), 3.32(1H, dd, J=5.0 Hz, J=11.2 Hz), 3.68(1H, dd, J=8.5 Hz, J=11.2 Hz), 3.95–4.10(1H, m), 4.25–4.35(1H, m), 4.41(1H, dd, J=7.5 Hz, J=11.2 Hz), 4.60(1H, dd, J=4.3 Hz, J=11.2 Hz), 8.09(1H, d, J=8.5 Hz), 8.27(1H, bs)

EXAMPLE 5

(4R)-N-[(1S)-1-Propyl-yl-2-nitroxyethyl]-2-oxothiazolidin-4-yl-carboxamide (Exemplary Compound No. 1-27)

0.84 g of the desired compound was obtained as colorless crystals in similar procedures to those in Example 4 by using 0.50 g of (4R)-2-oxothiazolidine-4-carboxylic acid and 0.75 g of (1S)-1-propyl-2-nitroxyethylamine hydrochloride.

m.p.: 99–100° C. (decomp.) NMR spectrum (d$_6$-DMSO) δ ppm: 0.87(3H, t, J=7.1 Hz), 1.15–1.55(4H, m), 3.32(1H, dd, J=4.8 Hz, J=11.2 Hz), 3.68(1H, dd, J=8.6 Hz, J=11.2 Hz), 4.03–4.18(1H, m), 4.23–4.33(1H, m), 4.39(1H, dd, J=7.5 Hz, J=11.2 Hz), 4.60(1H, dd, J=4.2 Hz, J=11.2 Hz), 8.09(1H, d, J=8.5 Hz), 8.27(1H, bs)

EXAMPLE 6
(4R)-N-[(1S)-1-Butyl-2-nitroxyethyl]-2-oxothiazolidin-4-yl-carboxamide (Exemplary Compound No. 1-71)

570 mg of the desired compound were obtained as colorless crystals in similar procedures to those in Example 4 by using 441 mg of (4R)-2-oxothiazolidine-4-carboxylic acid and 500 mg of (1S)-1-butyl-2-nitroxyethylamine hydrochloride.

m.p.: 110–112° C. (decomp.) NMR spectrum (CDCl$_3$) δ ppm: 0.91(3H, t, J=7.2 Hz), 1.20–1.43(4H, m), 1.45–1.75 (2H, m), 3.61(1H, dd, J=4.9 Hz, J=11.2 Hz), 3.83(1H, dd, J=8.6 Hz, J=11.2 Hz), 4.23–4.45(3H, m), 4.60(1H, dd, J=3.3 Hz, J=11.2 Hz), 6.65(1H, bs), 6.81(1H, d, J=8.6 Hz)

EXAMPLE 7
(4R)-N-[(1S)-1-Isopropyl-2-nitroxyethyl]-2-oxothiazolidin-4-yl-carboxamide (Exemplary Compound No. 1-59)

343 mg of the desired compound were obtained as colorless crystals in similar procedures to those in Example 4 by using 333 mg of (4R)-2-oxothiazolidine-4-carboxylic acid and 500 mg of (1S)-1-isopropyl-2-nitroxyethylamine hydrochloride.

m.p.: 89–91° C. NMR spectrum (d$_6$-DMSO) δ ppm: 0.96(3H, d, J=7.3 Hz), 1.00(3H, d, J=6.6 Hz), 1.83–2.02(1H, m), 3.64(1H, dd, J=4.0 Hz, J=11.2 Hz), 3.84(1H, dd, J=8.6 Hz, J=11.2 Hz), 4.05–4.20(1H, m), 4.35–4.52(2H, m), 4.65 (1H, dd, J=4.0 Hz, J=11.2 Hz), 6.80(1H, bs), 6.86(1H, d, J=9.2 Hz)

EXAMPLE 8
(4R)-N-[(1S)-1-Isobutyl-2-nitroxyethyl]-2-oxothiazolidin-4-yl-carboxamide (Exemplary Compound No. 1-83)

636 mg of the desired compound were obtained as yellow oil in similar procedures to those in Example 4 by using 544 mg of (4R)-2-oxothiazolidine-4-carboxylic acid and 500 mg of (1S)-1-isobutyl-2-nitroxyethylamine hydrochloride.

NMR spectrum (d$_6$-DMSO) δ ppm: 0.93(3H, d, J=6.6 Hz), 0.95(3H, d, J=7.9 Hz), 1.30–1.80(3H, m), 3.61(1H, dd, J=4.0 Hz, J=11.2 Hz), 3.82(1H, dd, J=8.6 Hz, J=11.2 Hz), 4.30–4.50(3H, m), 4.59(1H, dd, J=3.3 Hz, J=11.2 Hz), 6.69(1H, bs), 6.85(1H, d, J=7.9 Hz)

REFERENCE EXAMPLE 1
(4R)-N-[(1R)-1-Methyl-2-nitroxyethyl]-2-oxothiazolidin-4-yl-carboxamide In 100 ml of dry benzene were suspended 5.64 g of (4R)-2-oxothiazolidine-4-carboxylic acid, 6.7 ml of oxalyl chloride and a few drops of dimethylformamide were added thereto, and the mixture was stirred at room temperature for 3 hours. The solvent was distilled off under reduced pressure, further benzene was added thereto, and the suspension was distillated azeotropically to dryness to obtain the pale yellow acid chloride.

In 150 ml of dry dichloromethane were suspended 5.00 g of (1R)-1-methyl-2-nitroxyethylamine hydrochloride, 14 ml of triethylamine and a solution of the previously obtained acid chloride in 70 ml of dry dichloromethane were added dropwise thereto with stirring under ice-cooling, and the mixture was stirred under ice-cooling for 1 hour. Then, the solvent was distilled off under reduced pressure and the residue was purified by silica gel column chromatography employing cyclohexane-ethyl acetate (1:4) as an eluent to obtain pale yellow crystals. The crystals were recrystallized from ethyl acetate to obtain 2.79 g of the desired compound as colorless crystals.

m.p.: 101–102° C. (decomp.) NMR spectrum (CDCl$_3$+d$_6$-DMSO) δ ppm: 1.27(3H, d, J=6.9 Hz), 3.55–3.75(2H, m), 4.23–4.58(4H, m), 7.47(1H, d, J=7.1 Hz), 7.61(1H, s)

REFERENCE EXAMPLE 2
(1S)-N-(t-Butoxycarbonyl)-1-methyl-2-nitroxyethylamine

In 200 ml of dry acetonitrile were suspended 17.9 g of nitronium tetrafluoroboron, and 17.5 ml of 2,4,6-collidine were added dropwise thereto at −5° C. to 0° C. under a nitrogen stream. The reaction mixture was stirred at 0° C. for 30 minutes, 10.7 g of N-t-butoxycarbonyl-L-alaninol were added thereto, and the mixture was stirred at room temperature for 1 hour and 20 minutes. Then, the solvent was distilled off under reduced pressure and ethyl acetate was added to the residue. The insolubles were filtered off and the filtrate was evaporated to dryness under reduced pressure. The thus obtained yellow oil was purified by silica gel column chromatography employing cyclohexane-ethyl acetate (9:1) as an eluent to obtain 7.12 g of the desired compound as a colorless oil.

NMR spectrum (CDCl$_3$) δ ppm: 1.23 (3H, d, J=7.3 Hz), 1.45(9H, s), 3.90–4.15(1H, m), 4.27–4.75(3H, m)

REFERENCE EXAMPLE 3
(1S)-1-Methyl-2-nitroxyethylamine hydrochloride

In 80 ml of 4N hydrochloric acid-dioxane were dissolved 4.52 g of (1S)-N-(t-butoxycarbonyl)-1-methyl-2-nitroxyethylamine, and the mixture was left to stand at room temperature for 1 hour and 50 minutes. To the mixture were added 160 ml of ether, and the crystals were collected by filtration and dried to obtain 3.02 g of the desired compound as colorless crystals.

m.p.: 134–135° C. NMR spectrum (CDCl$_3$+d$_6$-DMSO) δ ppm: 1.47(3H, d, J=6.6 Hz), 3.55–3.70(1H, m), 4.65–4.80 (2H, m)

REFERENCE EXAMPLE 4
(1R)-N-(t-Butoxycarbonyl)-1-methyl-2-nitroxyethylamine 8.55 g of the desired compound were obtained as colorless oil in similar procedures to those in Reference example 2 by using 13.09 g of nitronium tetrafluoroboron and 7.72 g of N-t-butoxycarbonyl-D-alaninol.

NMR spectrum (CDCl$_3$) δ ppm: 1.23 (3H, d, J=7.3 Hz), 1.45(9H, s), 3.95–4.15(1H, m), 4.28–4.75(3H, m)

REFERENCE EXAMPLE 5
(1R)-1-Methyl-2-nitroxyethylamine hydrochloride 1.60 g of the desired compound were obtained as colorless crystals in similar procedures to those in Reference example 3 by using 8.55 g of (1R)-N-(t-butoxycarbonyl)-1-methyl-2-nitroxyethylamine and 90 ml of 4N hydrochloric acid-dioxane.

m.p.: 133–135° C. NMR spectrum (CDCl$_3$+DMSO-d6) δ ppm: 1.47(3H, d, J=6.9 Hz), 3.55–3.70(1H, m), 4.65–4.78 (2H, m)

REFERENCE EXAMPLE 6
(1S)-N-(t-Butoxycarbonyl)-1-ethyl-2-nitroxyethylamine 3.19 g of the desired compound were obtained as a pale yellow oil in similar procedures to those in Reference example 2 by using 4.00 g of nitronium tetrafluoroboron and 4.03 g of (1S)-N-(t-butoxycarbonyl)-1-ethyl-2-hydroxyethylamine.

NMR spectrum (CDCl$_3$) δ ppm: 0.98(3H, t, J=7.3 Hz), 1.40–1.70(2H, m), 1.45(9H, s), 3.70–3.95(1H, m), 4.20–4.70(3H, m)

REFERENCE EXAMPLE 7
(1S)-1-Ethyl-2-nitroxyethylamine hydrochloride 2.10 g of the desired compound were obtained as colorless crystals in similar procedures to those in Reference example 3 by using 3.19 g of (1S)-N-(t-butoxycarbonyl)-1-ethyl-2-nitroxyethylamine and 50 ml of 4N hydrochloric acid-dioxane.

m.p.: 121–123° C. (decomp.) NMR spectrum (d$_6$-DMSO) δ ppm: 0.96(3H, t, J=7.2 Hz), 1.50–1.80(2H, m), 3.35–3.50 (1H, m), 4.66(1H, dd, J=6.6 Hz, J=11.9 Hz), 4.81(1H, dd, J=4.0 Hz, J=11.9 Hz), 8.49(3H, bs)

REFERENCE EXAMPLE 8
(1S)-N-(t-Butoxycarbonyl)-1-propyl-2-nitroxyethylamine 3.03 g of the desired compound were obtained as colorless crystals in similar procedures to those in Reference example 2 by using 8.60 g of nitronium tetrafluoroboron and 7.49 g of (1S)-N-(t-butoxycarbonyl)-1-propyl-2-hydroxyethylamine.

m.p.: 57–58° C. NMR spectrum (CDCl$_3$) δ ppm: 0.95(3H, t, J=7.0 Hz), 1.25–1.70(4H, m), 1.45(9H, s), 3.80–4.05(1H, m), 4.20–4.70(3H, m)

REFERENCE EXAMPLE 9
(1S)-1-Propyl-2-nitroxyethylamine hydrochloride 2.77 g of the desired compound were obtained as colorless crystals in similar procedures to those in Reference example 3 by using 4.00 g of (1S)-N-(t-butoxycarbonyl)-1-propyl-2-nitroxyethylamine and 40 ml of 4N hydrochloric acid-dioxane.

m.p.: 157–158° C. (decomp.) NMR spectrum (d$_6$-DMSO) δ ppm: 0.89(3H, t, J=7.2 Hz), 1.30–1.70(4H, m), 3.40–3.55 (1H, m), 4.65(1H, dd, J=6.8 Hz, J=11.9 Hz), 4.81(1H, dd, J=3.4 Hz, J=11.9 Hz), 8.51(3H, bs)

REFERENCE EXAMPLE 10
(1S)-N-(t-Butoxycarbonyl)-1-butyl-2-nitroxyethylamine 1.56 g of the desired compound were obtained as a yellow oil in similar procedures to those in Reference example 2 by using 1.87 g of nitronium tetrafluoroboron and 2.09 g of (1S)-N-(t-butoxycarbonyl)-1-butyl-2-hydroxyethylamine.

NMR spectrum (CDCl$_3$) δ ppm: 0.91(3H, t, J=7.3 Hz), 1.25–1.65(6H, m), 1.45(9H, s), 3.83–3.98(1H, m), 4.30–4.60(3H, m)

REFERENCE EXAMPLE 11
(1S)-1-Butyl-2-nitroxyethylamine hydrochloride 702 mg of the desired compound were obtained as colorless crystals in similar procedures to those in Reference example 3 by using 1.56 g of (1S)-N-(t-butoxycarbonyl)-1-butyl-2-nitroxyethylamine and 15 ml of 4N hydrochloric acid-dioxane.

m.p.: 133–135° C. (decomp.) NMR spectrum (CDCl$_3$) δ ppm: 0.94(3H, t, J=7.3 Hz), 1.20–2.00(6H, m), 3.55–3.70 (1H, m), 4.65–4.85(2H, m)

REFERENCE EXAMPLE 12
(1S)-N-(t-Butoxycarbonyl)-1-isopropyl-2-nitroxyethylamine 3.07 g of the desired compound were obtained as a yellow oil in similar procedures to those in Reference example 2 by using 3.19 g of nitronium tetrafluoroboron and 3.31 g of (1S)-N-(t-butoxycarbonyl)-1-isopropyl-2-hydroxyethylamine.

NMR spectrum (CDCl$_3$) δ ppm: 0.97(3H, d, J=5.9 Hz), 0.99(3H, d, J=6.6 Hz), 1.45(9H, s), 3.65–3.80(1H, m), 4.35–4.63(3H, m)

REFERENCE EXAMPLE 13
(1S)-1-Isolropyl-2-nitroxyethylamine hydrochloride 1.97 g of the desired compound were obtained as colorless crystals in similar procedures to those in Reference example 3 by using 3.07 g of (1S)-N-(t-butoxycarbonyl)-1-isopropyl-2-nitroxyethylamine and 30 ml of 4N hydrochloric acid-dioxane.

m.p.: 174–175° C. (decomp.) NMR spectrum (CDCl$_3$) δ ppm: 1.14(3H, d, J=7.3 Hz), 1.17(3H, d, J=6.6 Hz), 2.10–2.30(1H, m), 3.40–3.52(1H, m), 4.70–4.90(2H, m)

REFERENCE EXAMPLE 14
(1S)-N-(t-Butoxycarbonyl)-1-isobutyl-2-nitroxyethylamine 3.84 g of the desired compound were obtained as a yellow oil in similar procedures to those in Reference example 2 by using 3.91 g of nitronium tetrafluoroboron and 4.35 g of (1S)-N-(t-butoxycarbonyl)-1-isobutyl-2-hydroxyethylamine.

NMR spectrum (CDCl$_3$) δ ppm: 0.93(3H, d, J=4.6 Hz), 0.95(3H, d, J=4.6 Hz), 1.20–1.50(2H, m), 1.45(9H, s), 1.60–1.80(1H, m), 3.90–4.10(1H, m), 4.25–4.65(3H, m)

REFERENCE EXAMPLE 15
(1S)-1-Isobutyl-2-nitroxyethylamine hydrochloride 2.32 g of the desired compound were obtained as colorless crystals in similar procedures to those in Reference example 3 by using 3.84 g of (1S)-N-(t-butoxycarbonyl)-1-isobutyl-2-nitroxyethylamine and 40 ml of 4N hydrochloric acid-dioxane.

m.p.: 174–175° C. (decomp.) NMR spectrum (CDCl$_3$) δ ppm: 0.93–1.10(6H, m) 1.50–1.70(1H, m), 1.72–2.00(2H, m), 3.65–3.82(1H, m), 4.63–4.85(2H, m)

TEST EXAMPLE 1

Collateral Vessel Dilating Action by Intravenous Administration

Beagle dogs (male) weighing 9 to 13 kg were anesthetized by intravenous injection of pentobarbital at a dose of 30 mg/kg and tested under artificial respiration. In order to measure the pressure of the left carotid artery, a polyethylene cannula (Atom intravenous catheter 2F) was inserted antegrade into one branch of the left thyroid artery. The left carotid artery upstream from this pressure measurement site was occluded for 1 minute with an arterial clamp, and the pressure immediately before occlusion (P) and the decrease in peripheral pressure (ΔP) were measured. Next, the test drug was administered through another polyethylene cannula inserted into the inguinal vein. The left carotid artery was occluded for 1 minute after 5, 15, 30, 45 and 60 minutes, and pressure immediately before occlusion (Pa) and the decrease in peripheral pressure (ΔPa) each time were measured. Collateral vessel dilating effect (Collateral CI) of the test drug was determined according to the following formula:

$$CI=100-(\Delta Pa/Pa)\times 100/(\Delta P/P)$$

As a result of this test, the compounds of Examples 1, 5, 6 and 8 exhibited an excellent action, CI(60) at the dose of 0.3 mg/kg being more then 10.

TEST EXAMPLE 2
Collateral Vessel Dilatincr Action by Administration into the Portal Vein While test specimens were prepared according to the method of Test example 1, the animal was laparotomized along the abdominal median line, and a branch of the mesenteric vein was removed and incised so as to administer the test drug into the portal vein. A polyethylene cannula (Atom intravenous catheter 2F) was inserted antegrade into this vein to reside in the portal vein, and then the test drug was administered through it. In order to test the first-pass effect of the test drug, it was first administered intravenously (inguinal vein) to determine collateral vessel dilating action of the drug for 60 minutes. The same test drug was then administered into the portal vein 2 or 3 hours later to determine collateral vessel dilating action for 60 minutes, and those actions were compared with each other.

As a result of this test, the compound of Example 1 exhibited an excellent collateral vessel dilating action.

TEST EXAMPLE 3

Inhibition of aspirin-induced ulcer

As a test animal, 10 Donryu strain male rats each weighing 200 g-250 g were used in one group. The rats were fasted before the experiment for 24 hours but they could freely drink water. The test compounds were suspended in 0.5% carboxymethyl cellulose (CMC) solution. Meanwhile, for a control group, 0.5% CMC solution was used.

The test compound was orally administered (0.1 ml/100 g body weight) to the rats and an aspirin solution (150 mg/ml: suspended in 0.5% CMC solution) was orally administered (0.1 ml/100 g body weight) to the rats 1 hour later. Four hours after the administration of the aspirin solution, the rats were sacrificed using carbon dioxide gas and the stomach of each rat was taken out. Into the stomachs were poured 10 ml of 1% formalin solution to allow the stomachs to expand, and the stomachs were immersed in 1% formalin solution in a beaker for about 15–20 minutes. Then, each stomach was cut along the greater curvature thereof and an area of the ulceration in the gastric mucosa was measured by means of an image analysis apparatus [Luzex-F: manufactured by Nireko Co., Ltd.]. The average value of the area of the ulceration of each group was calculated from the area of the ulceration of each rat and the inhibition rate was obtained by comparing the average value of the test group with that of the control group. The results are shown in Table 4.

TABLE 4

| Compound | Administered dose (mg/kg) | Inhibition rate (%) |
|---|---|---|
| Compound of Example 1 | 30 | 63.58*⁾ |
|  | 100 | 80.15**⁾ |
|  | 300 | 93.17**⁾ |

*⁾$p < 0.05$
**⁾$p < 0.005$

According to the present test, the compound of Example 1 exhibited excellent anti-ulcerative action.

TEST EXAMPLE 4

Stability of Compounds

About 2 mg of the test compound was accurately weighed and placed in a brown bottle. The bottle was left to stand at a dark place at room temperature (24–26° C.) for 4 weeks and a residual ratio (%) of the test compound was measured by high pressure liquid chromatography (column: Inertsil ODS-3, eluting solvent: 10 mM (pH=7.0) phosphoric acid buffer/acetonitrile=80/20). The results are shown in Table 5.

TABLE 5

| Compound | Residual ratio (%) |
|---|---|
| Compound of Example 1 | 101.2 |
| Compound A*) | 49.8**) |

*)1:1 Mixture of compound of Example 1 and the (4R), (1R)-isomer thereof
**)Compound of Example 1/the (4R), (1R)-isomer thereof = 2/1

According to the present test, the compound of Example 1 exhibited excellent storage stability as compared with that of 1:1 mixture of the compound of Example 1 and the (4R),(1R)-isomer thereof. Meanwhile, the compound of Example 1 exhibited excellent storage stability as compared with the (4R),(1R)-isomer.

TEST EXAMPLE 5

Stability of compounds

Approximately 20 mg of each of the test compounds and test mixtures of compounds were accurately weighed using a weighing bottle and said test compounds and test mixtures of compounds were then left to stand at 40° C. for 4 months in a 5000 ml desiccator containing approximately 500 g of silica gel. The residual amount of each compound was determined after 0, 1, 2 and 4 months by high pressure liquid chromatography (column: Chiralcel OD-H prepared by Daicel Chemical Inds. Ltd.; eluting solvent: hexane/2-propanol in a ratio of 17:3 by volume). The results are as shown in Table 6.

TABLE 6

| | | Residual Amount (%) | | | |
|---|---|---|---|---|---|
| No. | Compound | 0 Months | 1 Months | 2 Months | 4 Months |
| 1. | Compd. of Ex.1 | 100 | 100 | 100 | 97 |
| 2. | (4R),(1R)-isomer | 100 | 101 | 99 | 97 |
| 3. | 9:1 Mixture | 100(89/11) | 93(95/5) | 87(96/4) | 78(98/2) |
| 4. | 7:3 Mixture | 100(70/30) | 87(76/24) | 61(85/15) | 31(87/13) |
| 5. | 1:1 Mixture | 100(50/50) | 83(54/46) | 66(58/42) | 40(78/22) |

1. Test compound in Experiment No. 2 is the (4R),(1R)-isomer of the compound of Example 1.
2. "9:1 Mixture" means a 9:1 mixture of the compound of Example 1 and its (4R),(1R)-isomer.
3. "93(95/5)" means that the total amount of the compound of Example 1 and its (4R),(1R)-isomer present after 1 month is 93% of the original amount present and that the ratio of the compound of Example 1 to its (4R),(1R)-isomer is 95:5.

TEST EXAMPLE 6

Approximately 20 mg of each of the test compounds were accurately weighed using a weighing bottle and said test compounds were then left to stand at 60° C. for 7 days in a 5000 ml desiccator containing approximately 500 g of silica gel. The residual amount of each compound was determined after 0, 1, 2, 4, 6 and 7 days by high pressure liquid chromatography (column: L-Column ODS prepared by Kagakuhin Kensa Kyokai; eluting solvent: 0.04% aqueous phosphoric acid/methanol in a ratio of 9:1 by volume). The results are as shown in Table 7.

TABLE 7

| | | Residual Amount (%) | | | | | |
|---|---|---|---|---|---|---|---|
| No. | Compound | 0 days | 1 day | 2 days | 4 days | 6 days | 7 days |
| 1. | Compd. of Ex.1 | 100 | 100 | 99 | 96 | 84 | 60 |
| 2. | (4R),(1R)-isomer of Compd. of Ex.1 | 100 | 101 | 98 | 85 | 11 | 0 |

Taking Test Examples 4, 5 and 6 together, it is apparent that both the compound of Example 1 and its (4R),(1R)-isomer are more stable on storage than 1:1, 7:3 and 9:1 mixtures thereof, and that the compound of Example 1 is more stable than its (4R),(1R)-isomer.

PREPARATION EXAMPLE 1

| Capsule | |
| --- | --- |
| Compound of Example 1 | 50.0 mg |
| Lactose | 128.7 |
| Corn starch | 70.0 |
| Magnesium stearate | 1.3 |
| | 250 mg |

The thus formulated powder is mixed and passes through a sieve of 60 mesh, and then the powder is encapsulated in No. 3 gelatin capsule of 250 mg to prepare a capsule.

PREPARATION EXAMPLE 2

| Tablet | |
| --- | --- |
| Compound of Example 1 | 50.0 mg |
| Lactose | 124.0 |
| Corn starch | 25.0 |
| Magnesium stearate | 1.0 |
| | 200 mg |

The thus formulated powder is mixed and a 200 mg-tablet is made by means of a tablet making machine.

If necessary, sugar coating can be applied to the tablet.

We claim:

1. An optically active thiazolidinone compound having the formula:

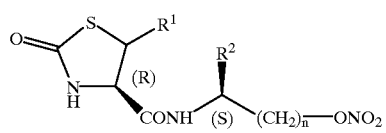

(I)

wherein:

$R^1$ represents a hydrogen atom, an alkyl group having from 1 to 4 carbon atoms, a phenyl group which is unsubstituted or is substituted by a substituent selected from the group consisting of alkyl groups having from 1 to 4 carbon atoms, alkoxy groups having from 1 to 4 carbon atoms and halogen atoms, or a phenylalkyl group wherein the alkyl group has 1 or 2 carbon atoms and the phenyl group is unsubstituted or is substituted by a substituent selected from the group consisting of alkyl groups having from 1 to 4 carbon atoms, alkoxy groups having from 1 to 4 carbon atoms and halogen atoms;

$R^2$ represents an alkyl group having from 1 to 6 carbon atoms; and n represents 1 or 2.

2. The optically active thiazolidinone compound according to claim 1, wherein $R^1$ is a hydrogen atom, an alkyl group having from 1 to 4 carbon atoms, a phenyl group which is unsubstituted or is substituted by a substituent selected from methyl groups, methoxy groups, fluorine atoms and chlorine atoms, a benzyl group which is unsubstituted or is substituted by a substituent selected from methyl groups, methoxy groups, fluorine atoms and chlorine atoms, or a phenethyl group which is unsubstituted or is substituted by a substituent selected from methyl groups, methoxy groups, fluorine atoms and chlorine atoms.

3. The optically active thiazolidinone compound according to claim 1, wherein $R^1$ is a hydrogen atom, a methyl group, a 4-methoxyphenyl group or a benzyl group.

4. The optically active thiazolidinone compound according to claim 1, wherein $R^1$ is a hydrogen atom.

5. The optically active thiazolidinone compound according to claim 1, wherein $R^2$ is an alkyl group having from 1 to 4 carbon atoms.

6. The optically active thiazolidinone compound according to claim 1, wherein $R^2$ is a methyl group, an ethyl group, a propyl group, an isopropyl group, a butyl group or an isobutyl group.

7. The optically active thiazolidinone compound according to claim 1, wherein $R^2$ is a methyl group, a propyl group, a butyl group or an isobutyl group.

8. The optically active thiazolidinone compound according to claim 1, wherein $R^2$ is a methyl group.

9. The optically active thiazolidinone compound according to claim 1, wherein n is 1.

10. The optically active thiazolidinone compound according to claim 1, wherein:

$R^1$ is a hydrogen atom, an alkyl group having from 1 to 4 carbon atoms, a phenyl group which is unsubstituted or is substituted by a substituent selected from methyl groups, methoxy groups, fluorine atoms and chlorine atoms, a benzyl group which is unsubstituted or is substituted by a substituent selected from methyl groups, methoxy groups, fluorine atoms and chlorine atoms, or a phenethyl group which is unsubstituted or is substituted by a substituent selected from methyl groups, methoxy groups, fluorine atoms and chlorine atoms;

$R^2$ is an alkyl group having from 1 to 4 carbon atoms; and n is 1.

11. The optically active thiazolidinone compound according to claim 1, wherein:

$R^1$ is a hydrogen atom, a methyl group, a 4-methoxyphenyl group or a benzyl group;

$R^2$ is a methyl group, an ethyl group, a propyl group, an isopropyl group, a butyl group or an isobutyl group; and n is 1.

12. The optically active thiazolidinone compound according to claim 1, wherein:

$R^1$ is a hydrogen atom;

$R^2$ is a methyl group, a propyl group, a butyl group or an isobutyl group; and n is 1.

13. The optically active thiazolidinone compound according to claim 1, wherein $R^1$ is a hydrogen atom and $R^2$ is a methyl group.

14. The optically active thiazolidinone compound according to claim 1, selected from the group consisting of:

(4R)-N-[(1S)-1-methyl-2-nitroxyethyl]-2-oxothiazolidin-4-yl-carboxamide;

(4R)-N-[(1S)-1-methyl-2-nitroxyethyl]-5-methyl-2-oxothiazolidin-4-yl-carboxamide;

(4R)-N-[(1S)-1-methyl-2-nitroxyethyl]-5-(4-methoxyphenyl)-2-oxothiazolidin-4-yl-carboxamide;

(4R)-N-[(1S)-1-methyl-2-nitroxyethyl]-5-benzyl-2-oxothiazolidin-4-yl-carboxamide;

(4R)-N-[(1S)-1-ethyl-2-nitroxyethyl]-2-oxothiazolidin-4-yl-carboxamide;

(4R)-N-[(1S)-1-propyl-2-nitroxyethyl]-2-oxothiazolidin-4-yl-carboxamide;

(4R)-N-[(1S)-1-propyl-2-nitroxyethyl]-5-methyl-2-oxothiazolidin-4-yl-carboxamide;

(4R)-N-[(1S)-1-propyl-2-nitroxyethyl]-5-(4-methoxyphenyl)-2-oxothiazolidin-4-yl-carboxamide;
(4R)-N-[(1S)-1-propyl-2-nitroxyethyl]-5-benzyl-2-oxothiazolidin-4-yl-carboxamide;
(4R)-N-[(1S)-1-butyl-2-nitroxyethyl]-2-oxothiazolidin-4-yl-carboxamide;
(4R)-N-[(1S)-1-butyl-2-nitroxyethyl]-5-methyl-2-oxothiazolidin-4-yl-carboxamide;
(4R)-N-[(1S)-1-butyl-2-nitroxyethyl]-5-(4-methoxyphenyl)-2-oxothiazolidin-4-yl-carboxamide;
(4R)-N-[(1S)-1-butyl-2-nitroxyethyl]-5-benzyl-2-oxothiazolidin-4-yl-carboxamide;
(4R)-N-[(1S)-1-isobutyl-2-nitroxyethyl]-2-oxothiazolidin-4-yl-carboxamide;
(4R)-N-[(1S)-1-isobutyl-2-nitroxyethyl]-5-methyl-2-oxothiazolidin-4-yl-carboxamide;
(4R)-N-[(1S)-1-isobutyl-2-nitroxyethyl]-5-(4-methoxyphenyl)-2-oxothiazolidin-4-yl-carboxamide; and
(4R)-N-[(1S)-1-isobutyl-2-nitroxyethyl]-5-benzyl-2-oxothiazolidin-4-yl-carboxamide.

15. (4R)-N-[(1S)-1-Methyl-2-nitroxyethyl]-2-oxothiazolidin-4-yl-carboxamide.

16. A composition for preventing or treating angina pectoris comprising an effective amount of an active compound in admixture with a pharmacologically acceptable carrier or diluent, wherein said active compound is an optically active thiazolidinone derivative according to claim 1.

17. A composition for preventing or treating angina pectoris comprising an optically active thiazolidinone compound of formula (I) as defined in claim 1 in admixture with its (4R),(1R)-isomer of the following formula (I')

(I')

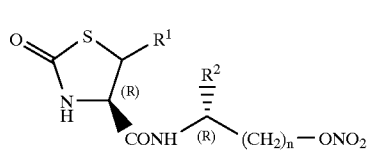

wherein $R^1$, $R^2$ and n are as defined in claim 1, and wherein the amount of the (4R),(1R)-isomer of the formula (I') is less than 10% by weight of the total amount of the composition.

18. The composition according to claim 17 comprising (4R)-N-[(1S)-1-methyl-2-nitroxyethyl]-2-oxothiazolidin-4-yl-carboxamide in admixture with (4R)-N-[(1R)-1-methyl-2-nitroxyethyl]-2-oxothiazolidin-4-yl-carboxamide, wherein the amount of the (4R)-N-[(1R)-1-methyl-2-nitroxyethyl]-2-oxothiazolidin-4-yl-carboxamide is less than 10% by weight of the total amount of the composition.

19. A method for the treatment or prophylaxis of angina pectoris comprising administering to a patient an effective amount of an active compound in admixture with a pharmacologically acceptable carrier or diluent, wherein said active compound is an optically active thiazolidinone compound according to claim 1.

20. A method for the treatment or prophylaxis of angina pectoris comprising administering to a patient an effective amount of an active compound in admixture with a pharmacologically acceptable carrier or diluent, wherein said active compound is (4R)-N-[(1S)-1-methyl-2-nitroxyethyl]-2-oxothiazolidin-4-yl-carboxamide.

21. A method for the treatment or prophylaxis of angina pectoris comprising administering to a patient an effective amount of an active ingredient in admixture with a pharmacologically acceptable carrier or diluent, wherein said active ingredient contains greater than 90% by weight of an optically active thiazolidinone compound of formula (I) as defined in claim 1 in admixture with less than 10% by weight of its (4R), (1R)-isomer of the following formula (I'):

(I')

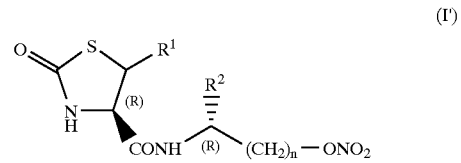

wherein $R^1$, $R^2$ and n are as defined in claim 1.

22. A process for preparing an optically active thiazolidinone compound according to claim 1 comprising reacting a carboxylic acid having the formula:

(III)

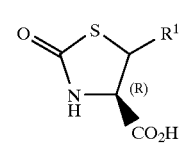

wherein $R^1$ is as defined in claim 1, or a reactive compound thereof with an amine having the formula:

(IV)

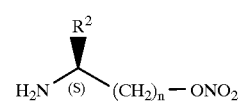

wherein $R^2$ is as defined in claim 1, or an acid addition salt thereof.

23. A process for preparing an optically active thiazolidinone compound according to claim 1 comprising reacting a carboxylic acid having the formula:

(III)

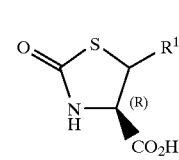

wherein $R^1$ is as defined in claim 1, or a reactive compound thereof with an amine compound having the formula:

(V)

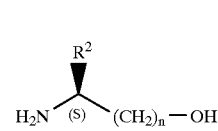

wherein $R^2$ is as defined in claim 1, or an acid addition salt thereof and then nitrating the compound thus obtained.

* * * * *